US008580528B2

(12) United States Patent
Verweij et al.

(10) Patent No.: US 8,580,528 B2
(45) Date of Patent: Nov. 12, 2013

(54) METHOD FOR PROGNOSTICATING THE CLINICAL RESPONSE OF A PATIENT TO B-LYMPHOCYTE INHIBITING OR DEPLETING THERAPY

(75) Inventors: Cornelis Lammert Verweij, Abcoude (NL); Paul-Peter Tak, Kortenhoef (NL)

(73) Assignee: Stichting VU-VUMC, Amsterdam (NL)

( * ) Notice: Subject to any disclaimer, the term of this patent is extended or adjusted under 35 U.S.C. 154(b) by 89 days.

(21) Appl. No.: 12/905,625

(22) Filed: Oct. 15, 2010

(65) Prior Publication Data

US 2011/0091457 A1    Apr. 21, 2011

Related U.S. Application Data

(60) Provisional application No. 61/252,517, filed on Oct. 16, 2009.

(51) Int. Cl.
*G01N 33/53* (2006.01)
(52) U.S. Cl.
USPC ........................................................ 435/7.21
(58) Field of Classification Search
None
See application file for complete search history.

(56) References Cited

U.S. PATENT DOCUMENTS

2010/0204058 A1* 8/2010 Chang et al. ............... 506/9
2010/0273671 A1* 10/2010 Lauwerys et al. .......... 506/9
2011/0091457 A1   4/2011 Verweij et al.

FOREIGN PATENT DOCUMENTS

| WO | WO 02/48310 | 6/2002 |
| WO | WO 2008/147206 | 12/2008 |
| WO | WO 2010/015632 | 2/2010 |
| WO | WO 2010/046503 | 4/2010 |
| WO | WO 2010/060999 | 6/2010 |

OTHER PUBLICATIONS

Huang Z., Pharmacology and Therapeutics, 2000, 86: 201-215.*
Sekiguchi et al., Rheumatology (2008) 47: 780-788.*
Crow M., Arthritis Research & Therapy 2010, 12(Suppl 1):S5, pp. 1-10.*
Scherer et al., Current Opinion in Rheumatology, 2010, 22: 237-245.*
Wong et al., Clin. Immunol., (2008) 126: 121-136.*
van der Pouw Kraan et al., Ann Rheum Dis. 2007, 66: 1008-1014.*
Koczan et al., Arthritis Research and Therapy 2008, 10:R50, p. 1-10.*
Landewe R., J. Rheumatol. 2007, 34 Suppl. 80: 8-15.*
Anolik et al., Immunol. Res. 2009, 45:144-158.*
Dreyling et al. 2009, Am Soc Hematol Educ Program. 542-551.*
Hartmann et al., Discov Med. 2009, 8:157-164.*
Hu et al., Clin Exp Immunol. 2009, 157:181-190.*
Karim et al., Rheumatology 2009, 48: 332-341.*
van Baarsen et al., Genes and Immunity 2006, 7: 522-531.*
Baechler et al., PNAS 2003, 100: 2610-2615.*
Verweij, C.L., "Transcript profiling towards personalized medicine in rheumatoid arthritis", The Netherlands Journal of Medicine 67(11):364- (2009).
Julia et al, "Identification of candidate genes for rituximab response in rheumatoid arthritis patients by microarray expression profiling im blood cells", Pharmacogenomics 10(10):1297-1308 (2009).
Mackay et al, "Selective dysregulation of the FcγIIB receptor on memory B cells in SLE", The Journal of Experimental Medicine 203(9):2157-2164 (2006).
Stürzebecher et al, "Expression profiling identifies responder and non-responder phenotypes to interferon-β in multiple sclerosis", Brain 126:1419-1429 (2003).
Vosslamber et al, "Pharmacological induction of interferon type I activity following treatment with rituximab determines clinical response in rheumatoid arthritis", Ann. Rheum. Dis. 70:1153-1159 (2011).
Jun'Ichi,, Sato, "Molecular Mechanisms Underlying Therapeutic Effects Of Interferon-Beta In Multiple Sclerosis", Japanese Journal of National Medical Services 57(7):441-455 (2003)—Abstract.
Serrano-Fernandez et al, "Gene expression profiling from blood samples of MS patients receiving interferon-Beta 1b therapy", Poster Abstracts, No. 0474, Tuesday, Nov. 8, 2005.
Singh et al, "Gene expression changes in peripheral blood mononuclear cells from multiple sclerosis patients undergoing β-interferon therapy", Journal of the Neurological Sciences 258:52-59 (2007).
Thurlings et al, "Relationship Between the Type I Interferon Signature and the Response to Rituximab in Rheumatoid Arthritis Patients", Arthritis & Rheumatism 62(12):3607-3614 (2010).
Thurlings et al, "The Type I IFN Signature Is a Negative Predictor of the Clinical Response to Rituximab Treatment in RA", Arthritis & Rheumatism vol. 60, Oct. 2009 Abstract Supplement, The 2009 ACR/ARHP Annual Scientific Meeting, Philadelphia, Oct. 16-21, 2009.
Mariette, Xavier, "Therapeutic Potential for B-Cell Modulation in Sjögren's Syndrome", Rheum. Dis. N. Am. 34:1025-1033 (2008).

* cited by examiner

*Primary Examiner* — Ilia Ouspenski
(74) *Attorney, Agent, or Firm* — Nixon & Vanderhye P.C.

(57) ABSTRACT

The invention relates to methods for predicting a clinical response to B-lymphocyte inhibiting or depleting therapies (BCIDT) using expression levels of genes of the Type I INF pathway. In another aspect, the invention relates to a method for evaluating a pharmacological effect of a treatment with B-lymphocyte inhibiting or depleting therapy. More in particular, the invention relates to a method for prognosticating the clinical response of a patient to treatment with a soluble BCID or TCID agent, said method comprising the steps of obtaining at least two samples from said patient wherein a first sample has not been exposed to a soluble BCID or TCID agent and wherein at least a second sample has been exposed to a soluble BCID or TCID agent, determining the level of an IFN-I type response in said at least two samples, comparing the level of the IFN-I type response in said first sample with the level of the IFN-I type response in said at least second sample and prognosticating said clinical response from said comparison.

16 Claims, 10 Drawing Sheets

Figure 1A:
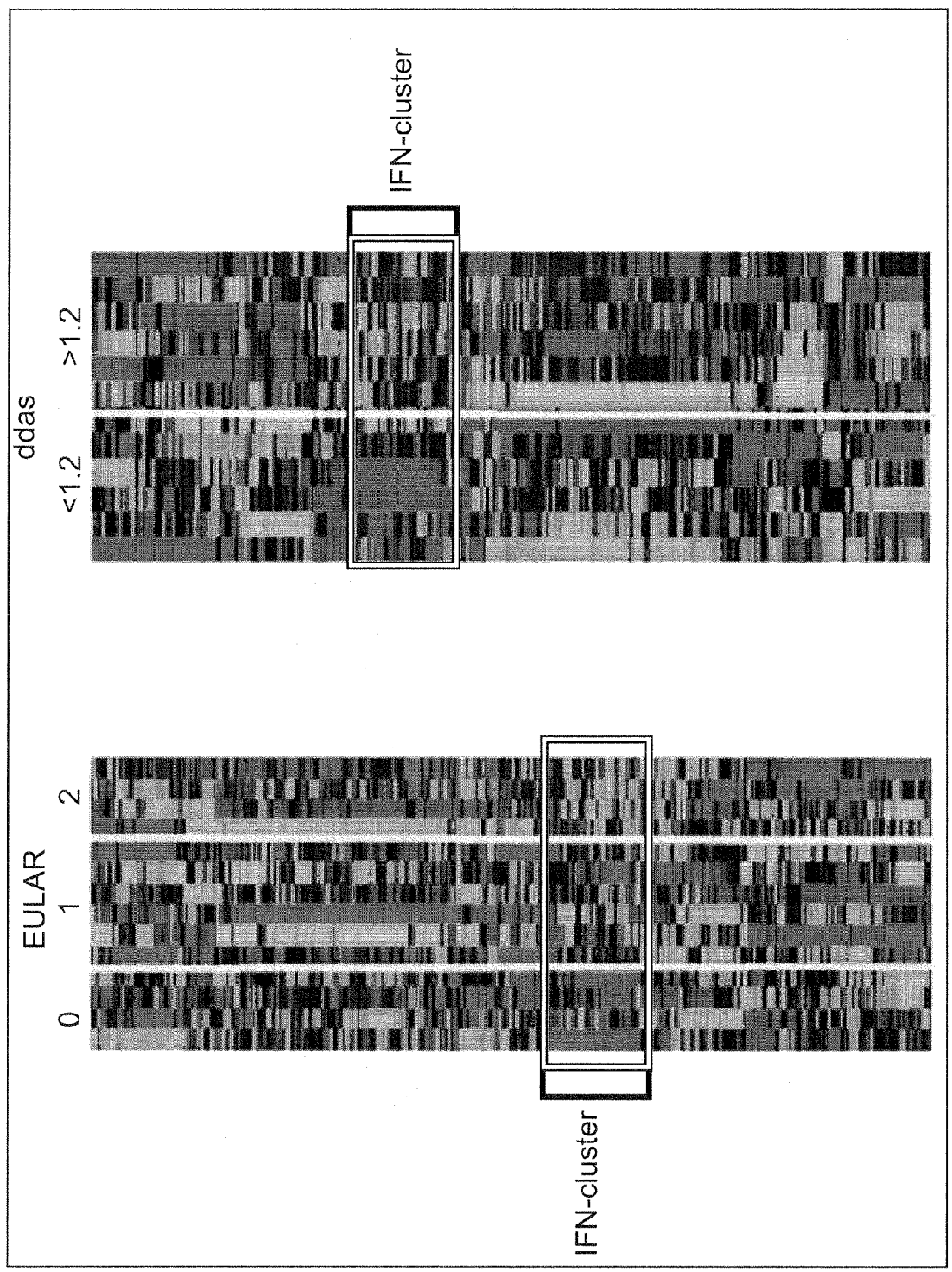

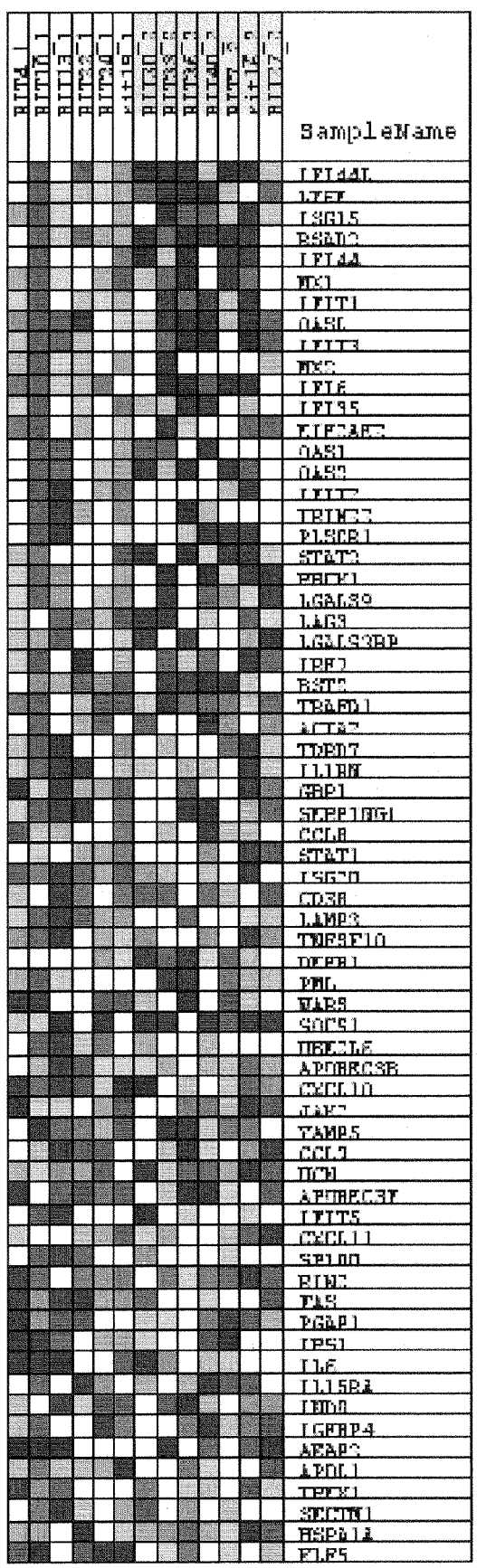
Fugure 1B:
Cluster diagram showing the genes that discriminate between ΔDAS28 responders and non-responders (the most informative ones are given in the window)

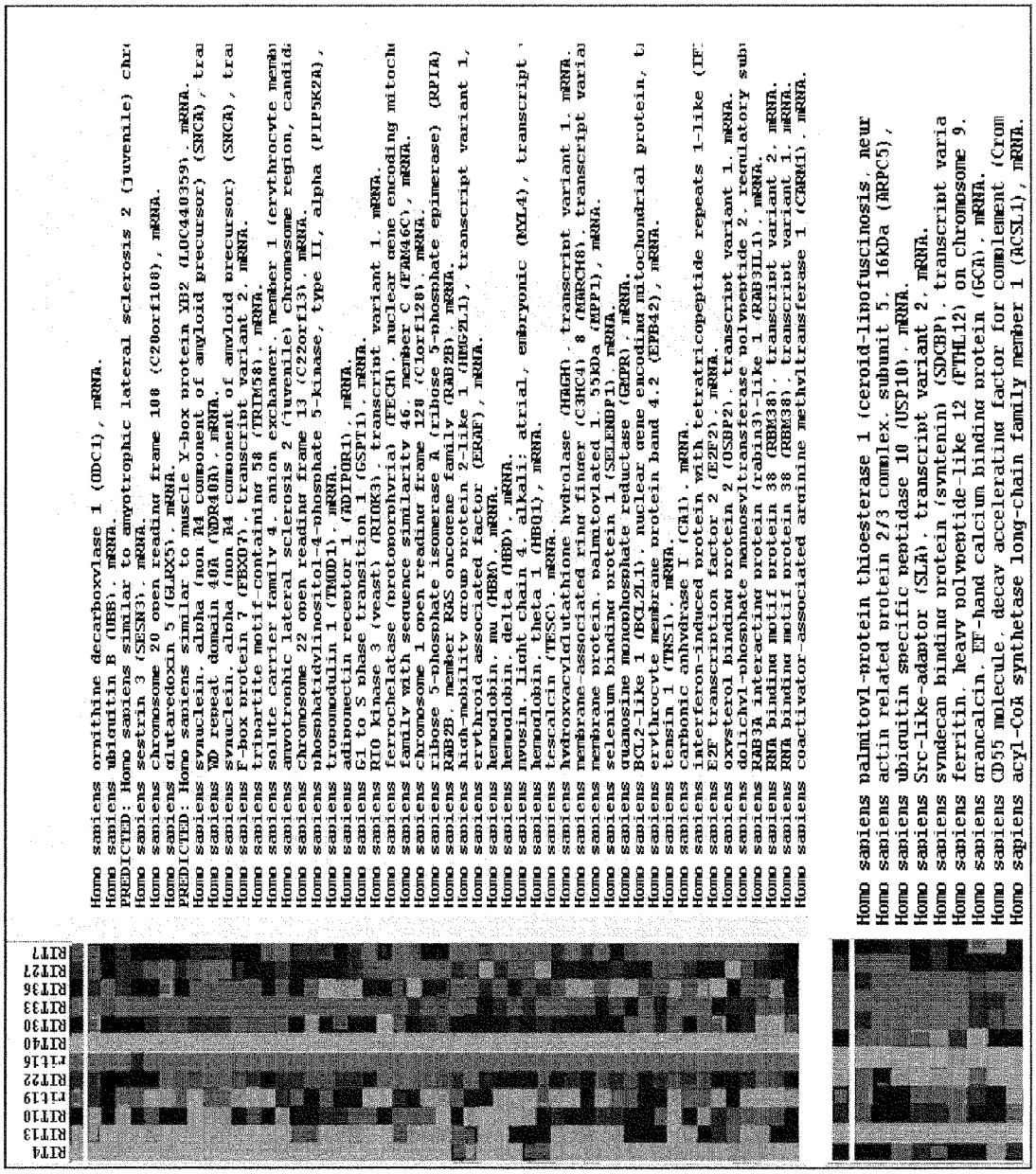
Fugure 1C:
Cluster of genes whose increased expression levels at baseline (represented in red) is associated with a good clinical response.

METHOD FOR PROGNOSTICATING THE CLINICAL RESPONSE OF A PATIENT TO B-LYMPHOCYTE INHIBITING OR DEPLETING THERAPY

RELATED APPLICATION

This application is based on and claims domestic priority benefits from U.S. Provisional application Ser. No. 61/252,517 filed Oct. 16, 2009, the entire content of which is expressly incorporated hereinto by reference.

FIELD

The invention relates to methods for predicting a clinical response to B-lymphocyte inhibiting or depleting therapies (BCIDT) using expression levels of genes of the Type I INF pathway. In another aspect, the invention relates to a method for evaluating a pharmacological effect of a treatment with B-lymphocyte inhibiting or depleting therapy. More in particular, the invention relates to a method for prognosticating the clinical response of a patient to treatment with a soluble BCID or TCID agent, said method comprising the steps of obtaining: i. one sample not exposed to a soluble BCID or TCID before the start of treatment with a soluble BCD or TCID, or ii, at least two samples from said patient wherein a first sample has not been exposed to a soluble BCID or TCID agent and wherein at least a second sample has been exposed to a soluble BCID or TCID agent. The prediction is based on determining the level of an IFN-I type response in said single sample and prognosticating said clinical response from said measurement.

Alternatively the prediction is based on determining the level of an IFN-I type response in said at least two samples, comparing the level of the IFN-I type response in said first sample with the level of the IFN-I type response in said at least second sample and prognosticating said clinical response from said comparison. This prediction rule can also be applied to prognosticate the response to type I IFNs.

BACKGROUND AND SUMMARY

BCIDT represent an important advancement in therapy for RA. However, there remains a proportion of patients who do not improve despite therapy. Although BCIDT have been shown to be highly efficient and safe for the treatment of RA patients, clinical complications have been reported for a subgroup of the treated patients. These include events associated with the first infusion (transient hyo- or hyper tension, pruritus and rash) and an increased incidence of infections (Cohen S. B. et al., Rituximab for rheumatoid arthritis refractory to anti-tumor necrosis factor therapy: Results of a multicenter, randomized, double blind, placebo controlled, phase III trial evaluating primary efficacy and safety at twenty-four weeks. Arthritis Rheum 2006, 54:2793-2806). These drugs are expensive and have the potential of serious toxicity. Therefore, it would be ideal to predict the patients who will respond, so that the use of these drugs can be targeted. Methods of predicting BCIDT response known in the art are based on observational, habitual or demographic variables (age, sex, disease activity score (DAS28) or health assessment questionnaire (HAQ) scores (Hydrich et al. Rheum 2006: 1558-1565). There is a need is for improved methods using personalised biological parameters. BCIDT have been implied for B- and T-cell, and auto-antibody—associated autoimmune diseases (AAID) such as multiple sclerosis (Hauser S. L. et al. B-cell depletion with rituximab in relapsing-remitting multiple sclerosis. N. Engl. J. med. 2008, 358; 676-688), Grave's disease (Fassi L. et al. Treatment of Grave's disease with rituximab specifically reduces the production of thyroid stimulating antibodies. Clin. Immunol. 2009, 130:352-358), Wegener's disease, Pemphigus Vulgaris (Ahmed A. R. et al., Treatment of pemphigus vulgaris with rituximab and intravenoud immuneglobulin. N. Engl. J. Med. 2006, 54:2970-2982; Mouquet et al., B-cell depletion immunotherapy in pemphigus: effects on cellular and humoral immune responses. J. Invest. Derm. 2008, 128:2859-2869), systemic lupus erythematosus (Gunnarsson I. et al., Histopathologic and clinical outcome of rituximab treatment in patients with cyclophosphamide-resistant proliferative lupus nephritis. Arth. Rheum 2007, 56:1263-1272; Guzman R. A. et al., Rituximab in refractory systemic lupus erythathosus. Lupus 2005, 14: 221 (OP18)), Sjogren's syndrome (Guzman R. A. et al, Rituximab in primary sjogren syndrome. J. Clin. Rheumatol. 2006, 12: 164 (s52)), some forms of vasculitis, some types of inflammatory muscle disease (Guzman R. A. et al., B cell depletion in poly-dermatomyositis. $6^{th}$ international Congress on Autoimmunity. Porto Portugal 2008 (URL kenes[dot]com[slash]autoimmunity)), systemic sclerosis, type I diabetes and immune and thrombotic thrombocytopenic purpura (Stasi R. Et al., Rituximab chimeric anti-CD20-monoclonal antibody treatment for adults with chronic idiopathic thrombocytopaenic purpura. Blood 2001, 98: 952-957). It is desirable to predict whether a patient will respond to BCIDT.

The invention relates to a method for prognosticating the clinical response of a patient to treatment with a soluble BCID or TCID agent, said method comprising the steps of a. Obtaining at least two samples from said patient wherein a first sample has not been exposed to a soluble BCID or TCID agent and wherein at least a second sample has been exposed to a soluble BCID or TCID agent
b. Determining the level of an IFN-I type response in said at least two samples,
c. Comparing the level of the IFN-I type response in said first sample with the level of the IFN-I type response in said at least second sample and
d. Prognosticating said clinical response from said comparison.

The method may also be performed by obtaining a sample that has not been exposed to soluble BCIDT or TCIDT before the start of therapy and prognosticate the clinical response by comparing the level of IFN response gene expression to a cut-off point The term "patient" refers to any subject (preferably human) afflicted with a disease likely to benefit from BCIDT, in particular a B-cell-related disease. B cells are the precursors of antibody-producing cells (plasma cells). In the process of undergoing activation and maturation into memory B cells and plasma cells they are very efficient antigen presenting cells (APCs) to T cells of soluble antigens that are bound specifically by the B cell antigen receptor (surface immunolglobuline). B cell ontogeny is characterized by a series of changing surface phenotypes. One of these is the CD20 surface marker (a 33-37 kDa membrane associated phosphoprotein) expressed during intermediate stages of development, which is lost during terminal differentiation to the immunoglobulin producing plasma cell. The exclusivity and high specificity of B-cell molecules like CD20 makes these types of proteins attractive pharmaceutical targets. Specifically beneficial features of CD20 are that free CD20 is not present in the circulation, CD20 does not modulate its own expression, and CD20 is not shed or internalised after antibody binding. Moreover, no endogenous CD20-like molecules are known that interfere with its function (Press et al., Monoclonal antibody 1F5 (anti-CD20) serotherapy of B-cell lymphomas. Blood 1987, 69:584-591). Diseases wherein B-cells directly contribute to pathogenesis and/or indirectly influence disease via changes in T cell function can be efficiently treated with BCIDT. B cell targeting via anti-CD20, e.g. rituximab (an anti-CD20 antibody), rapidly depletes peripheral blood CD20 positive B cells via complement-mediated and antibody dependent cell-mediated cytotoxicity (ADCC), induction of apoptosis and inhibition of cell growth (Maloney D. G. et al., Rituximab: Mechanism of action and resistance. Semin. Oncol. 2002, 29:2-9). B-cell levels usually reach a minimum by 1 month and repopulation generally starts by 6 months. Rituximab also downregulates CD40 ligand, CD40 and CD80, resulting in cganges to T cell function (Tokunaga M. Et al., Downregulation of CD40 and CD80 on B cells in patients with life-threatening systemic lupus erythematosus after successful treatment with rituximab. Rheumatology 2005, 44:176-182). It is not yet certain which of the possible mechanisms of action is most important in vivo. Interestingly, marked variability between individual responses have been observed, with a portion of patients failing to achieve a clinical response and others who reach a clinician remission for over 2 years.

In a preferred embodiment, said patient suffers from a disease selected from the group consisting of a B- or T-cell related disease, and an auto-antibody-associated autoimmune diseases (RAID). These diseases are likely to benefit from BCIDT.

Preferred diseases are selected from the group consisting of multiple sclerosis, systemic lupus erythematosus, Sjogren's syndrome, some forms of vasculitis, some types of inflammatory muscle disease, systemic sclerosis, type I diabetes and immune and thrombotic thrombocytopenic purpura, and transplant rejection or graft-versus-host disease, malignancy, a pulmonary disorder, an intestinal disorder, a cardiac disorder, a spondyloarthropathy, a metabolic disorder, anemia, pain, a hepatic disorder, and a skin disorder. In one embodiment, the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome. In another embodiment, said B- and T-cell, and auto-antibody-associated autoimmune diseases are selected from the group consisting of inflammatory bone disorders, bone resorption disease, periodontal disease. In still another embodiment, said B- and T-cell, and auto-antibody-associated autoimmune diseases are selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), psoriatic arthritis, and chronic plaque psoriasis.

In one embodiment of the invention, the B- and T-cell, and auto-antibody-associated autoimmune disease is Crohn's disease. In another embodiment, the disease is ulcerative colitis. In still another embodiment, the disease is psoriasis. In still another embodiment, the disease is psoriasis in combination with psoriatic arthritis (PsA).

In another preferred embodiment, said B- and T-cell, and auto-antibody-associated autoimmune disease comprises a disease which is likely to benefit from BCIDT. Preferably, said disease comprises type I diabetes.

In a preferred embodiment, said patient is an individual suffering from at risk or suffering from "Rheumatoid Arthritis (RA)" With the term an individual suffering from at risk or suffering from Rheumatoid Arthritis (RA) is meant an individual who is diagnosed with RA or is suspected by a doctor of suffering from RA or of developing the symptoms of RA within 10 years. Predominant symptoms of RA comprise pain, stiffness, and swelling of peripheral joints. The clinical manifestation of the disorder is very variable, ranging from mild, self-limiting arthritis to rapidly progressive multi-system inflammation with profound morbidity and mortality (Lee & Weinblatt 2001; Sweeney & Firestein 2004). RA symptoms may also comprise joint damage, which typically occurs early in the course of rheumatoid arthritis; 30 percent of patients have radiographic evidence of bony erosions at the time of diagnosis, and this proportion increases to 60 percent by two years (van der Heijde 1995; Br J. Rheumatol., vol. 34 Suppl 2, pp. 74-78). Typically, RA is a polyarthritis, which involves many joints (six or more), although for example in the early stages of the disease, only one or a few joints might be afflicted. Virtually all peripheral joints can be affected by the disease; however, the most commonly involved joints are those of the hands, feet and knees (Smolen et al, 1995; Arthritis Rheum., vol. 38, no, 1, pp. 38-43). In addition, RA can affect the spine, and atlanto-axial joint involvement is common in longer-standing disease, and constitutes a directly joint-related cause of mortality. Extra-articular involvement is another hallmark of RA, and this can range from rheumatoid nodules to life-threatening vasculitis (Smolen & Steiner 2003; Nat. Rev. Drug Discov., vol. 2, no. 6, pp. 473-488). RA can be classified using history, physical examination, laboratory and radiographic findings and this is usually performed according to criteria as described in Arnett F C, et al.: Arthritis Rheum 31:315, 1988. Preferably, said individual has a DAS28 score of 3.2 or higher. More preferably, said DAS28 score is 4.6 or higher. Most preferably, said DAS28 score is 5.1 or higher.

Patients who are resistant to methotrexate (MTX), usually considered first-line therapy for the treatment of RA, and/or failed to respond to TNF-blockers, are a further preferred group of patients for whom the method of the invention can be particularly useful.

More generally, patients who already receive a basic treatment for their TNF-related disease, e.g. with or without MTX, azathioprine or leflunomide, are particularly good candidates for the test method of the invention.

With the term "clinical response" is meant the clinical result of BCIDT. Said clinical response can be a positive or a negative clinical response. With a positive clinical response is meant that the severity of symptoms or the number of symptoms is reduced as a result of BCIDT or TCIDT. Preferably, said clinical result is the result of a treatment with a soluble TNF antagonist. When the disease is RA, it is preferred that a positive clinical response comprises at least reduction of swelling of joints. Preferably, an assessment of a clinical response is based on standardized and preferably validated clinical response criteria such as provided by the guidelines of organisations such as the National Institute for Health and Clinical Excellence (NICE), EULAR and/or ACR. Preferred clinical response criteria comprise DAS, DAS28 or the EULAR criteria or a combination thereof. In a preferred embodiment determination of a clinical response is based on an assessment using the DAS28 criteria. An advantage of the DAS28 is that it very sensitive to small effects of a therapy. Therefore, the method is very accurate when using DAS28 criteria.

Preferably, a positive clinical response is defined as a reduction in DAS28 score of at least 1.2 compared to the score of said individual prior to treatment with a soluble TNF antagonist. More preferably, a clinical response is based on assessment using EULAR criteria and DAS28 criteria.

Even more preferably, clinical response criteria are combined with demographic data, other clinical information or information about relevant habits. Demographic data comprise gender and/or age. Clinical information may comprise any relevant clinical observation or data. Preferred clinical information comprises CRP, ESR, ACPA titre, IgM RF titre, disease duration and medication. Information about relevant habits may be any relevant information. Preferred information comprises information about smoking habits.

B lymphocyte dysregulation with the production of rheumatoid factor (RF) and other autoantibodies, formation of immune complexes and release of destructive mediators are known to contribute to RA pathogenesis (Mannik M. and Nardella F. A., IgG rheumatoid factors and self-association of these antibodies, Clin. Rheum. Dis. 1985, 11:551-572). Approximately 80% of the RA patients develop RF antibodies. It is thought that B cells that produce RF migrate into the synovium and activate T cells by presentation of an antigen bound to IgG via HLA-DR4, via uptake by surface bound RF (Edwards J. C. W. and Cambridge G., Sustained improvement in rheumatoid arthritis following a protocol designed to deplete B lymphocytes. Rheumatology 2001, 40: 205-211). It was hypothesized that by eliminating this B cell antigen presentation to synovial T cells with anti-Cd20, T cell activation and T cell dependent synovial inflammation would decrease. In addition the ability of IgG RF B cells to self perpetuate, due to secretion of own antigen, provided rationale for the proposal that eradication of these cell clones may result in prolonged disease remission (Edwards J. C. W. et al., Do self-perpetuating B lymphocytes drive human auto-immune disease? Immunology 1999, 97:1868-1896).

The term "BCIDT" refers to molecules, such as proteins or small molecules, which can significantly reduce B cell function and/or number, and/or T cell function.

Preferably said BCIDT comprise anti-B cell antibodies, e.g. rituximab (Chimeric IgG1 Genentech/Biogen Approved 1997), $Y^{90}$-Ibritumomab tiuxetan (Murine (90Y) NHL Biogen/IDEC Low ADCC Approved 2002), $I^{131}$tositumomab (Murine (131I) NHL GSK Low CDC Approved 2003), Ofatumumab (Human IgG1 NHL/RA Genmab AC/GSK High CDC and ADCC Phase III trials), Ocrelizumab (Humanised IgG1 NHL/RA Genentech/Roche/Biogen Phase III trials), TRU-015 (SMIP # RA Trubion Pharma/Wyeth High ADCC Phase I/II Low CDC), Veltuzumab (Humanised NHL and ITP Immunomedics Phase I/II IgG1), AME-133v (Humanised IgG1 Relapsed NHL Applied Molecular High ADCC Phase I/II Evolution/Eli Lilly), PRO131921 (Humanised IgG1 CLL and NHL Genentech High CDC and ADCC Phase I/II (Version 114), GA10168 (Humanised CLL and NHL Glycart/Roche High PCD and ADCC Phase I/II), and anti-T cell antibodies e.g. Abatacept (recombinant fusion protein that selectively modulates CD80 and CD86-CD28 costimulatory signal required for full T cell activation), and alefacept (bivalent recombinant fusion protein consisting of a LFA-3 portion that binds CD2 receptors on T-cells, IgG1 portion of alefacept binds to Fc☐R receptor on natural killer cells to induce T-cell apoptosis).

Preferred therapies with soluble B and T-cell inhibitory or depleting molecules of the invention include, for example, rituximab, $Y^{90}$-Ibritumomab tiuxetan, $I^{131}$tositumomab, Ofatumumab, Ocrelizumab, and anti-T cell antibodies e.g. abatacept, and alefacept. More preferably, said soluble B and T-cell inhibitory or depleting molecule comprises rituximab.

With the term "sample" is meant any suitable sample comprising proteins or nucleotides. Preferred suitable samples include whole blood, saliva, faecal material, buccal smears, skin, and biopsies of specific organ tissues, such as muscle or nerve tissue and hair follicle, because these samples comprise relevant expression products. Preferably, said cell sample is a blood sample, because a blood sample is easy obtainable and comprises large amounts of relevant expression products.

With the term "IFN-I type response" is meant a response comprising the expression of an expression product of a gene involved in the IFN-I pathway. With the level of an IFN-I type response is meant the amount of expression product of any gene involved in the IFN-I response pathway.

An "expression product" of a gene is RNA produced from said genes or a protein produced from said RNA. The levels of the expression products may be determined separately for each different expression product or as a single measurement for more different expression products simultaneously. Preferably, the determination of the level of the expression products is performed for each different expression product separately, resulting in a separate measurement of the level of the expression product for each different expression product. This enables a more accurate comparison of expression levels of expression products with the expression levels of the same expression products in a control.

Determination of the level of the expression products according to methods of the invention may comprise the measurement of the amount of nucleic acids or of proteins. In a preferred embodiment of the invention, determination of the level of the expression products comprises determination of the amount of RNA, preferably mRNA. A level can be the absolute level or a relative level compared to the level of another mRNA. mRNA can be isolated from the samples by methods well known to those skilled in the art as described, e.g., in Ausubel at al., Current Protocols in Molecular Biology, Vol. 1; pp. 4.1.1-4.2.9 and 4.5.1-4.5.3, John Wiley & Sons, Inc. (1996). Methods for detecting the amount of mRNA are well known in the art and include, but are not limited to, northern blotting, reverse transcription PCR, real time quantitative PCR and other hybridization methods. The amount of mRNA is preferably determined by contacting the mRNAs with at least one sequence-specific oligonucleotide which hybridises to said mRNA. In a preferred embodiment said mRNA is determined with two sequence-specific oligonucleotides which hybridise to different sections of said mRNA. The sequence-specific oligonucleotides are preferably of sufficient length to specifically hybridize only to the RNA or to a cDNA prepared from said mRNA. As used herein, the term "oligonucleotide" refers to a single-stranded nucleic acid. Generally the sequence-specific oligonucleotides will be at least 15 to 20 nucleotides in length, although in some cases longer probes of at least 20 to 25 nucleotides will be desirable. Said sequence-specific oligonucleotides may also comprise non-specific nucleic acids. Such non-specific nucleic acids can be used for structural purposes, for example as an anchor to immobilise the oligonucleotides. The sequence-specific oligonucleotide can be labelled with one or more labelling moieties to permit detection of the hybridized probe/target polynucleotide complexes. Labelling moieties can include compositions that can be detected by spectroscopic, biochemical, photochemical, bioelectronic, immunochemical, and electrical optical or chemical means. Examples of labelling moieties include, but are not limited to, radioisotopes, e.g., 32P, 33P, 35S, chemiluminescent compounds, labelled binding proteins, heavy metal atoms, spectroscopic markers such as fluorescent markers and dyes, linked enzymes, mass spectrometry tags, and magnetic labels. Oligonucleotide arrays for mRNA or expression monitoring can be prepared and used according to techniques which are well known to those skilled in the art as described, e.g., in Lockhart et al., Nature Biotechnology, Vol. 14, pp. 1675-1680 (1996); McGall et al., Proc. Natl. Acad. Sci. USA, Vol. 93, pp. 13555-13460 (1996); and U.S. Pat. No. 6,040,138.

A preferred method for determining the amount of mRNA involves hybridization of labelled mRNA to an ordered array of sequence-specific oligonucleotides. Such a method allows the simultaneously determination of the mRNA amounts. The sequence-specific oligonucleotides utilized in this hybridization method typically are bound to a solid support. Examples of solid supports include, but are not limited to, membranes, filters, slides, paper, nylon, wafers, fibers, magnetic or non-magnetic beads, gels, tubing, polymers, polyvinyl chloride dishes, etc.

According to a preferred embodiment of the invention the determining the level(s) of the expression products is performed by measuring the amount of protein. The term "protein" as used herein may be used synonymously with the term "polypeptide" or may refer to, in addition, a complex of two or more polypeptides which may be linked by bonds other than peptide bonds, for example, such polypeptides making up the protein may be linked by disulfide bonds. The term "protein" may also comprehend a family of polypeptides having identical amino acid sequences but different post-translational modifications, particularly as may be added when such proteins are expressed in eukaryotic hosts. These proteins can be either in their native form or they may be immunologically detectable fragments of the proteins resulting, for example, from proteolytic breakdown. By "immunologically detectable" is meant that the protein fragments contain an epitope which is specifically recognized by e.g. mass spectrometry or antibody reagents as described below. Proteins levels can be determined by methods known to the skilled person, comprising but not limited to: mass spectrometry, Western blotting, immunoassays, protein expression assay, protein microarray etc.

A preferred embodiment of the invention provides a protein microarray (Templin at al. 2004; Comb. Chem. High Throughput Screen., vol. 7, no. 3, pp. 223-229) for simultaneous binding and quantification of the at least two biomarker proteins according to the invention. The protein microarray consists of molecules (capture agents) bound to a defined spot position on a support material. The array is then exposed to a complex protein sample. Capture agents such as antibodies are able to bind the protein of interest from the biological sample. The binding of the specific analyte proteins to the individual spots can then be monitored by quantifying the signal generated by each spot (MacBeath 2002; Nat. Genet, vol. 32 Suppl, pp. 526-532; Zhu & Snyder 2003; Curr. Opin. Chem. Biol., vol. 7, no. 1, pp. 55-63). Protein microarrays can be classified into two major categories according to their applications. These are defined as protein expression microarrays, and protein function microarrays (Kodadek 2001; Chem. Biol., vol. 8, no. 2, pp. 105-115). Protein expression microarrays mainly serve as an analytic tool, and can be used to detect and quantify proteins, antigen or antibodies in a biological fluid or sample. Protein function microarrays on the other hand can be used to study protein-protein, enzyme-substrate and small molecule-protein interactions (Huang 2003; Front Biosci., vol. 8, p. d559-d576). Protein microarrays also come in many structural forms. These include two-dimensional microarrays constructed on a planar surface, and three-dimensional microarrays which use a Flow-through support.

Types of protein microarray set-ups: reverse phase arrays (RPAs) and forward phase arrays (FPAs) (Liotta et al. 2003; Cancer Cell, vol. 3, no. 4, pp. 317-325). In RPAs a small amount of a tissue or cell sample is immobilized on each array spot, such that an array is composed of different patient samples or cellular lysates. In the RPA format, each array is incubated with one detection protein (e.g., antibody), and a single analyte endpoint is measured and directly compared across multiple samples. In FPAs capture agents, usually an antibody or antigen, are immobilized onto the surface and act as a capture molecule. Each spot contains one type of immobilized antibody or capture protein. Each array is incubated with one test sample, and multiple analytes are measured at once.

One of the most common forms of FPAs is an antibody microarray. Antibody microarrays can be produced in two forms, either by a sandwich assay or by direct labelling approach. The sandwich assay approach utilizes two different antibodies that recognize two different epitopes on the target protein. One antibody is immobilized on a solid support and captures its target molecule from the biological sample. Using the appropriate detection system, the labelled second antibody detects the bound targets. The main advantage of the sandwich assay is its high specificity and sensitivity (Templin, Stoll, Bachmann, & Joos 2004; Comb. Chem. High Throughput. Screen., vol. 7, no. 3, pp. 223-229). High sensitivity is achieved by a dramatic reduction of background yielding a high signal-to noise ratio. In addition, only minimal amounts of labelled detection antibodies are applied in contrast to the direct labelling approach were a huge amount of labelled proteins are present in a sample. The sandwich immunoassay format can also be easily amenable to the field of microarray technology, and such immunoassays can be applied to the protein microarray format to quantify proteins in conditioned media and/or patient sera (Huang et at 2001; Clin. Chem. Lab Med., vol. 39, no. 3, pp. 209-214; Schweitzer et at 2002; Nat Biotechnol., vol. 20, no. 4, pp. 359-365).

In the direct labelling approach, all proteins in a sample are labelled with a fluorophore. Labelled proteins that bind to the protein microarray such as to an antibody microarray are then directly detected by fluorescence. An adaptation of the direct labelling approach is described by Haab and co-workers (Haab, Dunham, & Brown 2001; Genome Biol., vol. 2, no. 2, p). In this approach, proteins from two different biological samples are labelled with either Cy3 or Cy5 fluorophores. These two labelled samples are then equally mixed together and applied to an antibody microarray. This approach, for example, allows comparisons to be made between diseased and healthy, or treated and untreated samples. Direct labelling has several advantages, one of which is that the direct labelling method only requires one specific antibody to perform an assay.

Miniaturized and multiplexed immunoassays may also used to screen a biological sample for the presence or absence of proteins such as antibodies (Joos et al. 2000; Electrophoresis, vol. 21, no. 13, pp. 2641-2650; Robinson et al. 2002; Nat. Med., vol. 8, no. 3, pp. 295-301).

In a preferred embodiment of the invention, the detection or capture agents such as the antibodies are immobilized on a solid support, such as for example on a polystyrene surface. In another preferred embodiment, the detection or capture agents are spotted or immobilized in duplicate, triplicate or quadruplicate onto the bottom of one well of a 96 well plate.

In a method according to the invention, a first sample is tested that has not been exposed to a soluble BCIDT and/or TCIDT. The level of an IFN-I type response of this sample is determined as a control sample. The level of an IFN-I type response of this sample is compared to the level of an IFN-I type response of a second sample from said individual. It is preferred that the first sample and the second sample are of the same tissue.

It is required that the second sample has been exposed to BCIDT and/or TCIDT. A sample from an individual who had received said soluble BCID and/or TCID treatment can be used.

Moreover, for response prediction a cell sample from an untreated individual can be used wherein said cell sample has been contacted with a soluble BCID or TCID agent in vitro. It is preferred that all samples have been provided with the same soluble BCID or TCID agent.

Accordingly, it is possible to perform a method according to the invention wherein said at least a second sample has been contacted with soluble BCID or TCID agents in vitro, whereas said first of said samples has been provided with a soluble BCID or TCID agent. This method is also preferred. An advantage thereof is that an in vitro culture with a soluble BCID or TCID agent is technically easier to perform. When a cell sample is used from an individual who had been treated with a soluble BCID or TCID agent, it is preferred to use a sample that is collected at some time after said individual had been exposed to said soluble BCID or TCID agent to allow said soluble BCID or TCID agent to interact with said sample and to allow INF type I genes to respond to said soluble BCID or TCID agent. Preferably, a cell sample is used which is collected between 1 and 4 months after the first exposure to said soluble BCID or TCID agent. More preferably, a cell sample which is collected between at 1-3 months after exposure is used, because at said time points, differences between good and poor responders are greater. Expression of genes involved in the type I IFN pathway reaches its peak around 3 months after starting a treatment with a soluble BCID or TCID agent. It is preferred that at least two cell samples are collected between 1 and 4 months after exposure to a soluble BCID or TCID agent is used, because more samples from different time points increases the accuracy of the method. Most preferably, a cell sample collected at 1, 2, 3 and 4 months after exposure to soluble BCID or TCID agent is used.

When using a cell sample from an individual who did not receive an a treatment with said soluble soluble BCID or TCID agent, said cell sample is preferably exposed to a soluble BCID or TCID agent under in vitro conditions. For in-vitro culturing conditions, said cell sample is preferably a blood sample. Preferably, said conditions comprise culturing cells. Culturing procedures for different cell types are well known in the art and a skilled person will be able to select a suitable procedure for the selected cell types.

A method of the invention is also suited to prognosticate the clinical response of an individual to said soluble BCID or TCID agent, prior to starting a treatment of said individual. To this end, the first sample is tested that has not been exposed to a soluble BCID or TCID agent. An advantage thereof is that such method can be used to determine the prospect of a positive clinical response in individuals before the start of BCIDT and/or TCIDT. The level of an IFN-I type response of this sample from the said individual is determined.

Moreover, a method of the invention is also suited to prognosticate the clinical response of an individual to said soluble BCID or TCID agent, prior to starting a treatment of said individual if at least two samples are cultured in vitro, in the presence and absence of a soluble BCID or TCID agent. It is understood that if the method is performed using in-vitro exposure of a sample, said first and said second samples may have been collected as a single sample which is split into a first and a second sample. An advantage thereof is that such method can be used to determine the prospect of a positive clinical response in individuals before the start of BCIDT or TCIDT.

It is preferred that said soluble BCID or TCID agent is allowed to interact with said cells and to allow genes involved in the type I IFN pathway to respond to the soluble BCID or TCID agent before measuring expression levels of said genes. Preferably, a preferred moment for measuring said expression levels is when the response of said genes is at its peak. A skilled person will be able to establish the most suitable moment to do this by culturing a cell sample taken from an individual prior to therapy with a soluble BCID or TCID agent. Preferably, culturing conditions comprise culturing in the presence of a soluble BCID or TCID agent for 24 to 48 hours. Preferably, said samples comprise blood cells. Preferably, said sample comprises whole blood.

In the present invention we show that some RA patients display a significant difference in the peripheral blood gene expression level of IFN type I response genes in association with a significant difference in the magnitude of the treatment-induced expression of type I IFN-response genes.

In a method according to the invention, an individual has a increased prospect of a positive clinical response to a treatment with a soluble BCID or TCID agent if expression levels of the expression products of IFN response genes of a said treatment are low prior to the start of treatment or are higher compared to the levels of the same expression products of said first sample. A increased prospect of a positive clinical response to a treatment with soluble soluble BCID or TCID agent is thus by a low level of expression products of IFN response genes in the first sample taken prior to the start of therapy, and/or increased if the in-vitro by a soluble BCID or TCID agent induced expression of IFN response genes is increased compared to levels of the same products of said first sample.

However, in another group of treated RA patients an increased level of expression of IFN-response genes is observed in the first sample taken prior of the strat of rituximab treatment. Especially RA patients that showed a poor clinical response to treatment showed an increase in IFN-response gene expression levels before the start of treatment and a decreased or no difference in IFN-response gene expression levels compared to that of sample one of the same individual after treatment with rituximab.

The present invention confirms the existence of both regulatory routes since some RA patients actively increase and others decrease their type I IFN-response genes upon rituximab.

In summary, this study shows that there is a large variation in the change of IFN-response gene expression levels before and after therapy with soluble BCID or TCID agents between RA patients. Interestingly, increased levels of gene products of type I IFN response genes or treatment-induced downregulation or an expression of IFN response genes which is not significantly different from that in the first sample take prior to the start of in-vivo or in-vitro administration of rituximab is associated with a poor clinical response to rituximab treatment. Monitoring of the IFN-response genes Mx1, ISG15, BAFF, DARC, OAS1, LGALS3BP, Mx2, OAS2 and SERPING1 before and after the start of rituximab is useful for early determination of clinical response to treatment. Consequently, the opposite effect of that observed with a good clinical response to rituximab. Hence, low levels of type I IFN response gene activity and an in-vivo or in-vitro induced upregulation of IFN response genes is associated with a good clinical response to a soluble BCID or TCID agent.

An expression level is classified as increased at baseline, i.e. prior to the start of therapy with a soluble BCID or TCID agent when said expression level of said expression product of said first sample is statistically significantly increased in said individual compared to the level of the same expression product found in a sample of a healthy control individuals. The term "significantly" or "statistically significant" refers to statistical significance and generally means a two standard deviation (SD) above normal, or higher, or below, or lower concentration of the expression product. In preferred embodiments, said difference is classified as statistically significant if the expression level is at least a 20 percent increased compared to expression level of the same expression product in control individuals. Preferably, the increase or decrease is at least 20, 25, 30, 35, 40, 45, 50, 75, 100, 150, 200 or 250 percent. Most preferably, said increase or decrease is at least 100 percent.

An expression level is also classified as different when said expression level of said expression product of said second sample is statistically significantly increased or decreased in said individual compared to the level of the same expression product found in said first sample. The term "significantly" or "statistically significant" refers to statistical significance and generally means a two standard deviation (SD) above normal, or higher, or below, or lower concentration of the expression product. In preferred embodiments, said difference is classified as statistically significant if the expression level is at least a 20 percent increased or decreased compared to expression level of the same expression product in control individuals. Preferably, the increase or decrease is at least 20, 25, 30, 35, 40, 45, 50, 75, 100, 150, 200 or 250 percent. Most preferably, said increase or decrease is at least 100 percent.

More preferred is a method, wherein said IFN-I type response level is determined by determining in said first sample or at least two samples the level of an expression product of at least one gene of Table 2. An advantage thereof is that these genes are more predictive. More preferably, 2, 3, 4, 5, 6, 7, 8, 9, 10, 11, 12, 13, 14, 15, 20, 25, 30 or 34 genes of Table 2 are used, because the inclusion of more genes of this table improves the accuracy of the method.

More preferred is a method, wherein one level of said IFN-I type response is determined by determining the level of an expression product of at least ISG15, Mx1, OAS1, LGALS3BP, RSAD2, IFI44L, MX2, OAS2, BAFF, DARC and/or SERPING1. An advantage thereof is that these genes have a good predictive power.

In a preferred embodiment of the invention, said IFN-I type response is determined by determining the level of an expression product of at least OAS1, ISG15 and Mx1. An advantage thereof is that these use of these genes results in a good predictive power.

In another preferred embodiment of the invention, said IFN-I type response is determined by determining the level of an expression product of at least OAS1, ISG15 and Mx1. These genes have a good predictive power.

Even more preferred is an embodiment, wherein said IFN-I type response is determined by further determining the level of an expression product of at least Mx1, OAS1, and ISG15. An advantage thereof is that the combined use leads to an improved predictive power.

Another preferred embodiment is a method wherein said IFN-I type response is determined by determining the level of an expression product of at least Mx1, LGALS3BP, RSAD2, OAS1, ISG15, and IFI44L. More preferably, said IFN-I type response is determined by determining the level of an expression product of at least Mx1, OAS1, ISG14, LGALS3BP, Mx2, OAS2 and SERPING1.

More preferably said IFN-I type response is determined by determining the level of an expression product of at least the 15 validation genes listed in Table 2 and 3, and BAFF and DARC. This further improves the predictive power of the method. Most preferred is a method wherein at least the 34 genes listed (Van der Pouw Kraan C. T. M. at al., Rheumatoid arthritis subtypes identified by genomic profiling of peripheral blood cells: assignment of a type I interferon signature in a subpopulation of patients. Annals of rheumatic Dis. 2007, 66:1008-1014).

In another aspect, the invention relates to a method for prognosticating a clinical response of a patient to a treatment with a soluble BCD or TCID agent, said method comprising determining the level of the expression products of the genes listed in Table 2 and 3, and BAFF and DARC in the said first sample prior to the start of therapy with soluble BCID or TCID agent, or at least two samples of said individual, wherein a first of said samples has not been exposed to a soluble BCID or TCID agent and wherein at least a second of said samples has been exposed to a soluble BCID or TCID agent prior to determining said level, said method further comprising comparing said levels and prognosticating said clinical response from said comparison.

More preferred is a method wherein said at least one gene comprises 2, 3, 4, 5, 6, 7, 8, 9, 10, 11, 12, 13, 14, 15, 16, 17, 18, 19, 20 or 21 genes of Table 2 and 3, and BAFF and DARC.

More preferred is a method wherein said at least two samples comprise cell samples. An advantage thereof is that cells samples comprise nucleic acids, which can advantageously be used for determining said levels of an IFN-I type response, said level of expression product of said genes and/or said at least one gene listed in Table 2 and 3, and BAFF and DARC.

More preferred is a method wherein second sample is of an individual between 1 and 4 months after the first exposure of said individual to said soluble BCID or TCID agent. An advantage thereof is that within this period, said IFN-I type response level or said level of the expression products of Table 3 differs significantly compared to said first sample.

In another aspect the invention relates to a method for treatment of a patient with a soluble BCID or TCID agent, comprising determining a prognosis for a clinical response to a treatment with said soluble BCID or TCID agent, further comprising treating said individual with said soluble soluble BCID or TCID agent, if said individual has been prognosticated as a good responder.

In another aspect, the invention relates to use of a soluble BCD or TCID agent for the preparation of a medicament for the treatment of a patient, wherein prior to said treatment a prognosis for a clinical response to said soluble BCID or TCID agent was determined with any of the methods described above.

In another aspect, the invention relates to an improved pharmacodynamic marker (PD marker) for evaluating a pharmacological effect of a treatment with a soluble BCID or TCID agent. Good PD markers are needed to improve the prediction of the efficacy and safety of a treatment with a soluble BCID or TCID agent at the individual patient level. These quantitative PD markers should reflect features of drug exposure and drug response with respect to modulation of the molecular target, the cognate biochemical pathways and/or downstream biological effects. The availability of quantitative PD markers provides a rational basis for decision making during e.g. treatment optimization. A PD marker currently described for rituximab is peripheral blood B cell levels. Various reasons for inadequate depletion have been proposed, including genetic polymorphisms of the FcRyIIIa gene (Anolik J. H. et al., The relationship of FCyRIIIa genotype to the degree of B cell depletion by rituximab in the treatment for systemic lupus eruthematosus. Arthritis Rheum 2003, 48:455-459) or defective complement. Other PD markers include levels of RF and autoantibodies against citrullinated are described to be downregulated in patients treated with soluble BCID or TCID agent who show a clinical response (Cambridge G. Et al., Serologic changes following B lymphocyte depletion therapy for rheumatoid arthritis. Arthritis Rheum 2003, 48: 2146-2154). Synovial biopsy studies suggested that the clinical response was associated with degree of B cell depletion in the synovial per se, but not in synovial plasma cell numbers and immunoglobuline production (Thurlings R. M. et al. Synovial tissue response to rituximab: mechanism of action and identification of biomerkers of response. Ann. Rheum. Dis. 2008, 67: 917-925). However, neither fully explains the response status. Moreover, most of the described PD markers are assessed by using mean levels of patient groups while most of these markers are not affected in each individual patient.

The invention provides a method for evaluating a pharmacological effect of a treatment of a patient with a soluble BCID or TCID agent said method comprising determining the level of an expression product of at least one gene of Table S2 in at least two samples of said individual, wherein a first of said samples has not been exposed to a soluble BCID or TCID agent and wherein at least a second of said samples has been exposed to said soluble BCID or TCID agent prior to determining said level. The method is preferably used to determine whether moment of renewed therapy and dose of a soluble BCID or TCID agent which a patient receives is well timed and sufficiently high to achieve an effect or a clinical response. Whether a clinical response can be achieved depends also on other factors. The method can also be used to determine whether the dose of a soluble BCID or TCID agent which a patient receives is not too high and might therefore cause side effects. With the term "pharmacological effect" is meant a biochemical or physiological effect of a soluble BCID or TCID agent. Preferably, such pharmacological effect is specific for a treatment with a soluble BCID or TCID agent. Preferably, such pharmacological effect reflects the relationship between an effective dose and the clinical response. Preferably, said effective dose is the dose as measured in the blood level. With the term "evaluating" is meant that results of a pharmacological effect is determined and used for decision making steps regarding further treatment. Preferably, evaluating comprises evaluating the dose, the efficacy and/or the safety of said soluble BCID or TCID agent. Preferably, the expression products of at least 2, 3, 4, 5, 6, 7, 8, 9, 10, 15, 25, genes of Table 2 and 3 and BAFF and DARC are used in the method. Other terms used are explained above. Preferably, the expression products of said genes comprises the genes, wherein the level of said expression product is higher than 1.5, 1.6, 1.7, 1.8, 1.9, 2.0, 2.1, 2.2, 2.4, 2.6 or 3.0, or lower than 0.68, 0.67, 0.66, 0.65, 0.64, 0.62 or 0.60 (see column "fold change", Table 2 and 3 and BAFF and DARC). Values equal or lower than T3 values and in "fold change" and reaching baseline expression values in Table 2 and 3 and BAFF and increased DARC are indicative of renewed administration and eventually increased dose of a soluble BCID or TCID agent. Values higher than 1 in "fold change" and resembling 13 values as listed in Table 2 and 3 and BAFF and DARC are indicative of an prolonged renewal of treatment. Upregulation of a gene having a "fold change" higher than 1 as listed in table 3 is indicative of an effective dose of a soluble BCID or TCID agent. In another preferred embodiment, said at least one gene comprises preferably genes and gene products that are responsive to type I IFN. See table 2 for further details on the mentioned genes. Preferred is a method wherein at least said second of said samples has been exposed to a soluble BCID or TCID agent prior to determining said level Another preferred is a method wherein at least said second of said samples has been exposed to a soluble BCID or TCID agent prior to determining said level.

An advantage of this method is that said level of at least one gene of Table 2 and 3 and BAFF and DARC reflects a good clinical response to a therapy with a soluble BCID or TCID agent. Therefore, said response reflects drug activity and can be used to monitor drug efficacy at the individual patient level. Drug efficacy is the ability of a drug to produce the desired therapeutic effect.

In another aspect, the invention relates to a method for treatment of a patient with a soluble BCID or TCID agent, wherein the dose of said soluble BCID or TCID agent treatment is based on results obtained by a method for evaluating a pharmacological effect of a treatment of a patient with a soluble BCID or TCID agent said method comprising determining the level of a pharmacogenomic response of at least one gene of Table 2 and 3 and BAFF and DARC in at least two samples of said individual, wherein a first of said samples has not been exposed to a soluble BCID or TCID agent and wherein at least a second of said samples has been exposed to a soluble BCID or TCID agent prior to determining said level. The term "based on" means that results of said method are taken into account in establishing the dose of said a soluble BCID or TCID agent most suited for the individual patient. Preferred is a method wherein a patient is treated with a soluble BCID or TCID agent and wherein said method for evaluating a pharmacological response is based on results obtained by a method for evaluating a pharmacological effect wherein said at least a second of said samples has been exposed to a soluble BCID or TCID agent prior to determining said level.

In another aspect, the invention relates to use of a soluble BCID or TCID agent for the preparation of a medicament for the treatment of an patient, wherein said wherein said treatment is evaluated based on a method for evaluating a pharmacological effect of a treatment of a patient with a soluble BCID or TCID agent said method comprising determining the level of a pharmacogenomic response of at least one gene of table 2 and BAFF and DARC in at least two samples of said individual, wherein a first of said samples has not been exposed to a soluble BCID or TCID agent and wherein at least a second of said samples has been exposed to said a soluble BCD or TCID agent prior to determining said level. Another preferred embodiment is the use of a soluble BCID or TCID agent for the preparation of a medicament for the treatment of a patient and wherein said method for evaluating a pharmacological response is based on results obtained by a method for evaluating a pharmacological effect wherein said at least a second of said samples has been exposed to a soluble BCID or TCID agent prior to determining said level.

In another aspect, the invention relates to a kit suitable for use in the above method, comprising up to 34 reagents, sequence specific oligonucleotides and/or capture agents for detecting up to 34 of the gene products listed (Van der Pouw Kraan C. T. M. et al., Rheumatoid arthritis subtypes identified by genomic profiling of peripheral blood cells: assignment of a type I interferon signature in a subpopulation of patients. Annals of rheumatic Dis. 2007, 66:1008-1014).

and of the genes listed in Table 2 and 3.

In another aspect, the invention relates to a kit suitable for use in the above method, comprising up to table 2 and 3 and BAFF and DARC.

FIGURE LEGENDS

FIG. 1A. Supervised hierarchical cluster analysis based on EULAR and ΔDAS28.

Relation between baseline gene expression and clinical response in 15 RA patients. RA patients were divided based on their clinical response to rituximab. Subsequently the peripheral blood gene expression profile at baseline (T0) was associated with the clinical response to treatment (EULAR and ΔDAS28).

Patients with a low level of IFN-response gene activity at baseline displayed a better clinical response to treatment as assessed by EULAR (A) and ΔDAS28 responses measured after 6 months. A good clinical response to TNF blockade is accompanied with a low level of IFN response gene activity at baseline.

FIG. 1B: Supervised hierarchical cluster analysis which reveals the IFN genes that discriminate responders from non-responders.

FIG. 1C: Clusters of protein metabolism genes whose increased expression levels at baseline (represented in red) are associated with a good clinical response.

Figure 2:
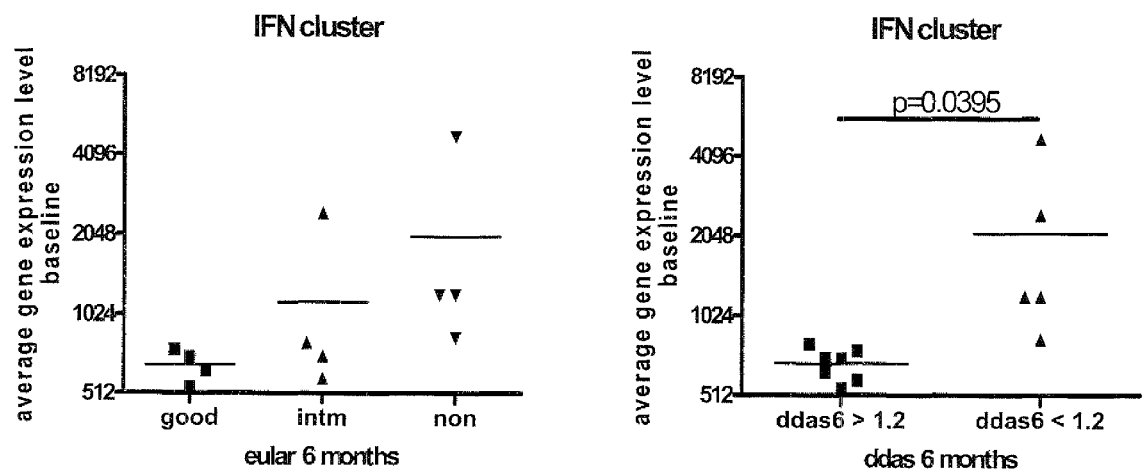

FIG. 2: Relation between IFN-signature at baseline and decrease in DAS28 score at 6 months.

Patients (n=12) were separated in EULAR good, moderate and poor responserds, and an ΔDAS28<1.2 en ΔDAS28>1.2 group. Subsequently the association with baseline IFN gene expression activity (mean table 2 genes) (y-axis) was determined (T-test; P=0.0395).

Figure 3:
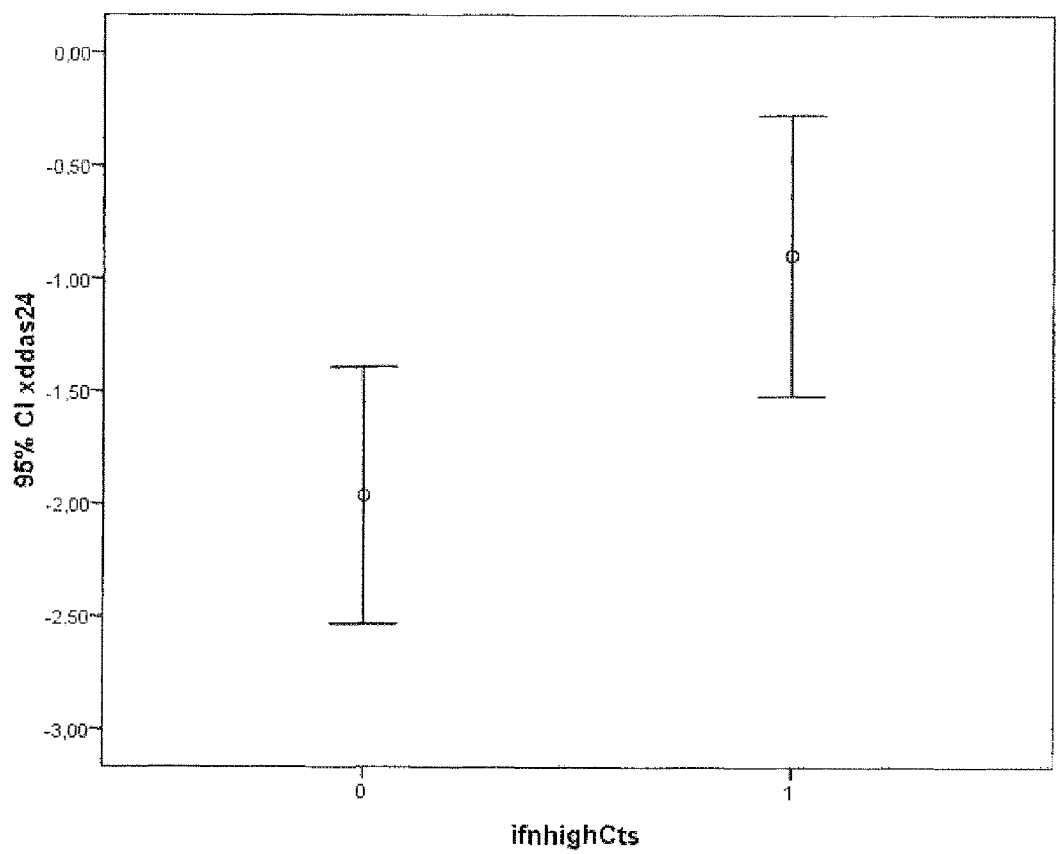

FIG. 3: Relation between IFN-signature at baseline and decrease in DAS28 score at 6 months.

Patients (n=50) were separated in an IFNhigh (0) and IFN low (1) group (x-axis). Subsequently the association with a change in DAS28 score (y-axis) was determined (linear regression; P=0.012).

Figure 4:
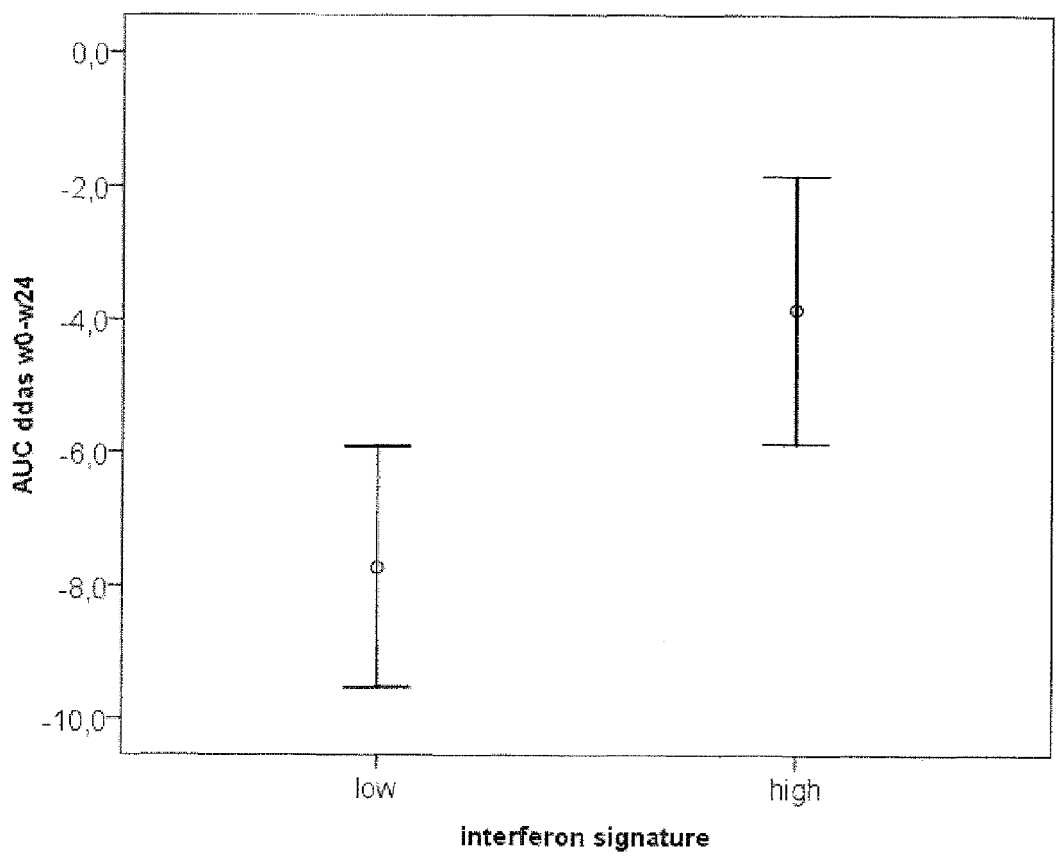

FIG. 4: Relation between IFN-signature at baseline and area under the curve (AUC) of decrease in DAS28 score at 6 months.

Patients (n=50) were separated in an IFNhigh (0) and IFN low (1) group (x-axis). Subsequently the association with the AUC of a change in DAS28 score (y-axis) was determined (linear regression; P=0.005).

Figure 5:
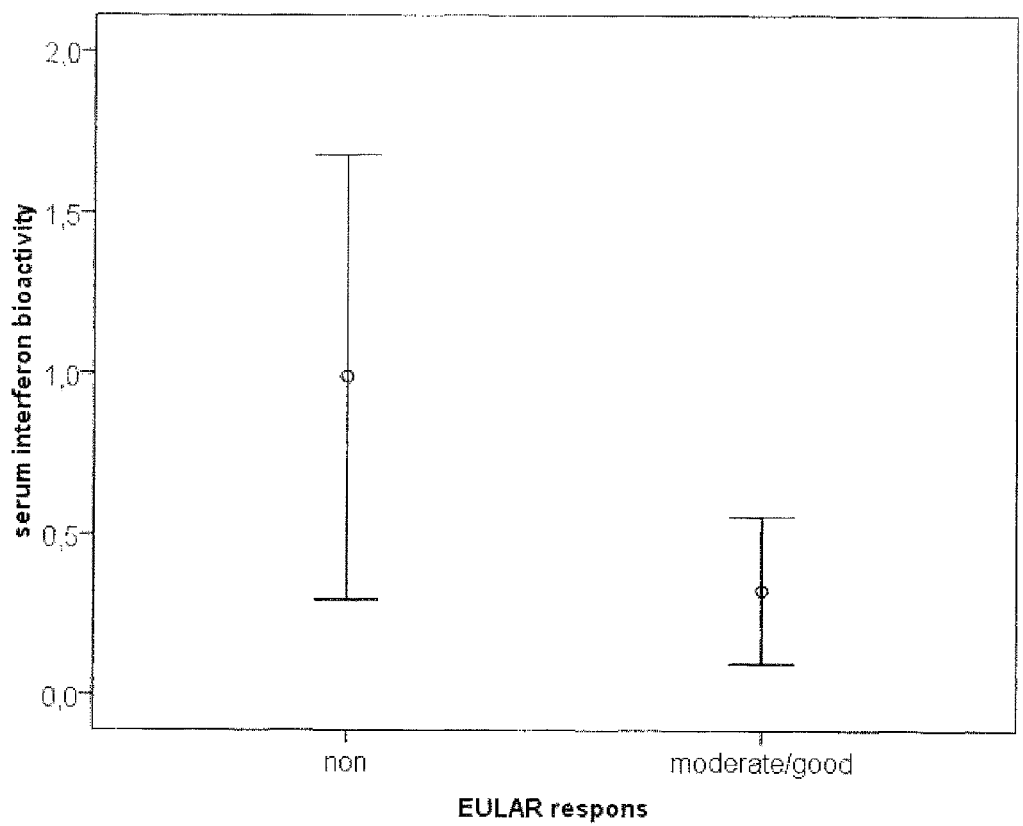

FIG. 5: Relation serum IFN bioactivity and EULAR response (n=30).

Patients (n=30) were separated in a non-responder and a moderate/good responder group. Successively, IFn bioactivity (y-axis) was measured. The association between responder status and IFN bioactivity was measured (P=0.027).

Figure 6:
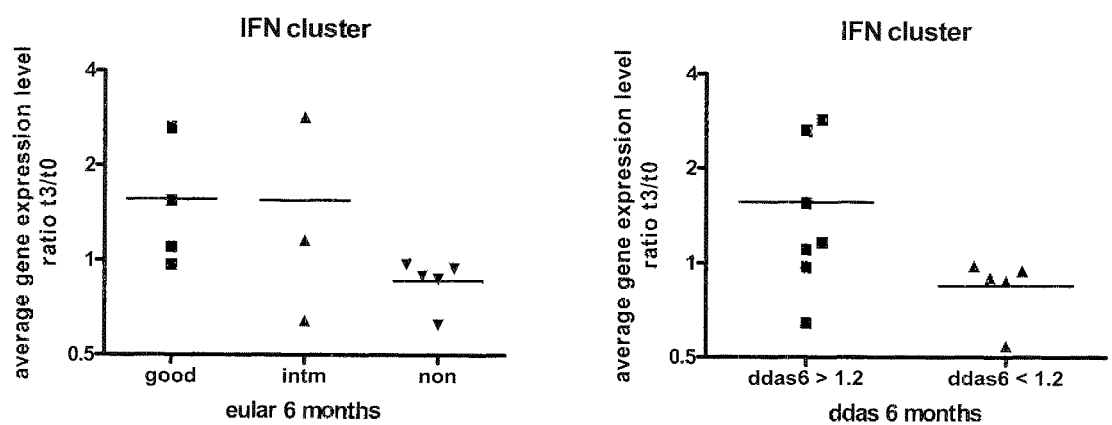

FIG. 6: Association between changes in IFN response signature at 3 months (T3) vs. baseline (T0) and clinical response (EULAR and ΔDAS28).

Patients (n=12) were separated in EULAR good, moderate and poor responserds, and an ΔDAS28<1.2 en ΔDAS28>1.2 group. Subsequently the association with T3/T0 expression ratio of IFN gene expression activity (based on table 3 genes) (y-axis) was compared to baseline levels in relation to clinical response to treatment (EULAR and ΔDAS28).

Patients with an upregulation in IFN-response genes at 3 months after the start of rituximab displayed a better clinical response to treatment as assessed by EULAR (A) and ΔDAS28 (B) response. Patients with a downregulated type I IFN response gene expression level revealed a poor clinical response to rituximab treatment.

Figure 7:
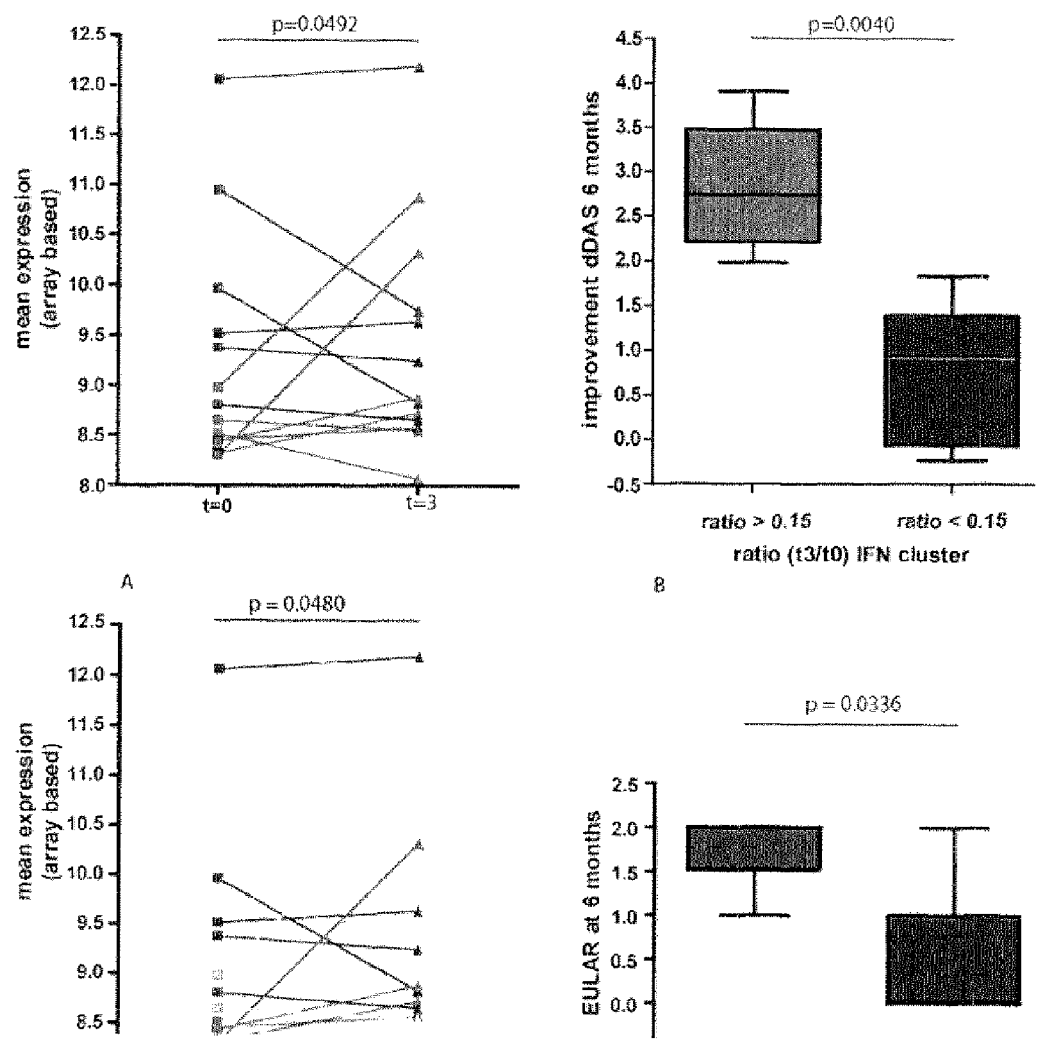

FIG. 7: Differential regulation of a set of 6 type I IFN-response genes upon rituximab therapy. The expression levels of 6 type I IFN-response genes were determined by cDNA-microarray analysis in peripheral blood cells of 13 RA patients before (t=0) and 3 months after (t=3) rituximab treatment. For each patient the expression levels were averaged (in log 2 space) and t=0 levels were compared to t=3 levels. (A and C) Gene expression over time is shown in green for patients with a good clinical response (?DAS>1.2 (A) or EULAR (C)), in red for the patients who exhibited a poor response (?DAS<1.2 (A) or EULAR (C)) and in blue for the patients who exhibited a moderate response (EULAR (C). T-test analysis revealed a significant increase in the expression of the type I IFN-response genes in responders compared to non-responders. (B and D) Patients were divided into two groups based on changes in gene expression levels of the type I IFN-response gene set (ratio < or >0.15). The groups were compared to each other with respect to ?DAS28 improvement (B) or EULAR responders state (D, 0=non responder, 1=moderate responder and 2=good responder).

Data are shown as box-plots; each box showed the 25th to 75th percentiles. This cut-off point marked a significant classification between clinical response status of the patients.

Figure 8:
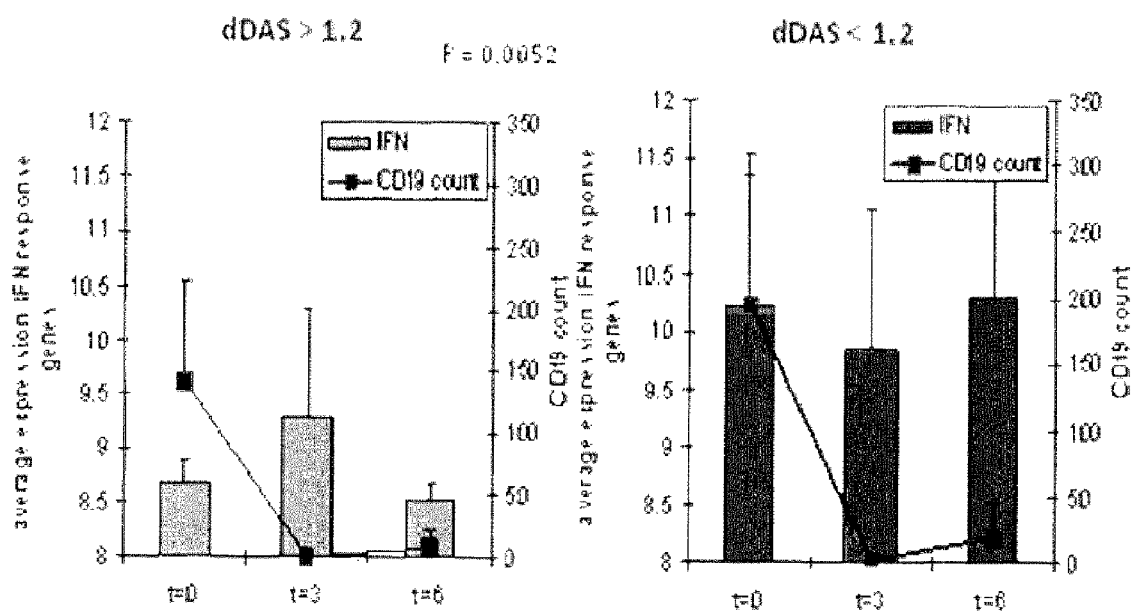

FIG. 8: Dynamics of the CD20 B-cell counts and type I IFN-response signature during rituximab treatment. Expression levels of type I IFN-related gene expression level (left y-axis) and B-cell counts (right y-axis) at baseline, 3 (t=3) and 6 months (t=6) in responders and non-responders based on ?DAS. Baseline type I IFN-response gene expression levels were significantly different between good-responders (DAS >1.2 or EULAR) and non-responders (DAS <1.2) (p=0.0052). In both groups, gene expression levels return to baseline values 6 months post therapy. No differences in B-cell count between groups are observed.

EXAMPLES

Example 1

Predicting a Clinical Response in RA Patients Treated with Infliximab Materials & Methods Patients Consecutive patients with RA according to the ACR criteria were enrolled in the study at the Jan van Breemen Institute (JvBI) and the department of Clinical Immunology and Rheumatology from the Academic Medical Center (AMC) in Amsterdam and the department of Rheumatology of the University Medical Center Utrecht. Inclusion criteria were; 18-85 years of age, a failure of at least two disease modifying anti-rheumatic drugs (DMARDs) including methotrexate (MTX), and active disease (DAS28≥3.2). Patients with who failed on previous use of a TNF blocking agent were included. Patients were on stable maximally tolerable MTX treatment. From the 15 patients of the JvBI whole blood samples (2.5 ml) were obtained using PAXgene tubes (PreAnalytix, GmbH, Germany) from 15 RA patients prior to initiation of therapy with rituximab (3 mg/kg intravenously at baseline, after x weeks). After 3 and 6 months of treatment another PAXgene tube was obtained. All patients gave written informed consent and the study protocol was approved by the Medical Ethics Committee of the respective centers. From the 20 patients of the AMC and the 30 patients from UMCU peripheral blood mononuclear cells from baseline were collected. After 24 weeks of treatment the clinical response to treatment was assessed using both the EULAR criteria (24; 25) as well as the reduction in DAS28 of at least 1.2 (26).

Blood Sampling for RNA Isolation

PBMCs were isolated from heparanized blood according standard protocols. 2.5 ml blood was drawn in PAXgene blood RNA isolation tubes (PreAnalytix, GmbH, Germany) and stored at −20° C. Tubes were thawed for 2 hours at room temperature prior to RNA isolation. Next, total RNA was isolated using the PAXgene RNA isolation kit according to the manufacturer's instructions including a DNAse (Qiagen, Venlo, Netherlands) step to remove genomic DNA. Quantity and purity of the RNA was tested using the Nanodrop spectrophotometer (Nanodrop Technologies, Wilmington, Del. USA).

Microarray Analysis

Quantity of the RNA was measured using the Nanodrop spectrophotometer (Nanodrop Technologies, Wilmington, Del.) and purity was determined using lab-on-chip technology (Agilent 2100 Bioanalyzer, Californie, USA).

The Illumina® TotalPrep™ RNA amplification kit (Ambion) was used to synthesize biotine labeled cRNA from 500 ng total RNA. Concentration of the labeled cRNA was measured using Nanodrop spectrophotometer and 750 ng biotinylated cRNA was hybridized onto the HumanHT-12 v3 Expression BeadChip (Illumine).

Amplification and hybridization were performed at the outsourcing company ServiceXS (Leiden, the Netherlands).

Microarray Data Analysis

Statistical analysis on microarray data was performed using Significant Analysis of Microarray data (SAM). Genes defined by a q-value (FDR) less than 5% were considered significantly different.

Cluster analysis was used to filter out differently expressed genes and for the subclassification of patients and coordinately expressed genes. Treeview was used to visualize differently expressed genes.

IFN-Response Gene Set

Previously, we showed that a prominent cluster of highly correlated type I IFN-response genes were upregulated in a subgroup of biological-naïve RA patients compared to healthy controls (6). A gene set consisting of 34 type I IFN-response genes was obtained from this data Van der pouw Kraan C. T. M. et al. Ann Rheum Dis 2007, 66:1008-1014).

Quantitative Real-Time PCR

RNA (0.5 µg) was reverse transcribed into cDNA using the Revertaid H-minus cDNA synthesis kit (MBI Fermentas, St. Leon-Rot, Germany) according to the manufacturer's instructions. Quantitative real-time PCR was performed using an ABI Prism 7900HT Sequence detection system (Applied Biosystems, Foster City, Calif., USA) using SybrGreen (Applied Biosystems). Primers were designed using Primer Express software and guidelines (Applied Biosystems). To calculate arbitrary values of mRNA levels and to correct for differences in primer efficiencies a standard curve was constructed. Expression levels of target genes were expressed relative to 18SRNA.

Statistical Analysis

Data was analyzed using software programs Graphpad Prism 4 (Graphpad Software, Inc., La Jolla, Calif.) and Statistical Package for Social Sciences version 14.0 (SPSS; Chicago, Ill.). First data was checked for normal (Gaussian) distribution. Two-group comparisons were analyzed using the independent sample T test, the Mann-Whitney U test or two-way ANOVA analysis where appropriate. The relationship of Q-PCR data with the clinical response (at week 24) was analyzed using regression analysis.

Data were considered significant with p-values less than 0.05.

Results

Pharmacogenomic Response to Rituximab Treatment

We investigated pharmacological changes on gene expression by peripheral blood cells of RA patients treated with rituximab. Therefore, we analysed the peripheral blood gene expression profiles of 15 RA patients at baseline (t=0) and three (t=3) and six (t=6) months after the start of therapy using the illumina micro array platform. Two class paired analysis using Significance Analysis of Microarraydata (SAM) at a False Discovery Rate (FDR) of less than 5% between pre- and post therapy data was applied to identify genes that were significantly changed in expression after rituximab therapy. This analysis revealed a set of 16 genes that was significantly down regulated after three months. At six months following therapy only 6 genes were still significantly down regulated (table 1).

As anticipated, all significantly regulated genes were B cell markers or B cell related genes indicative of an effective decrease of $CD20^+$ B cells in these patients at three months and a gradual rise in B cells after 6 months of therapy. Detailed analysis of the expression of specific B cell markers, such as CD19, revealed that the expression after three months of therapy reached a similar bottom level in all patients treated irrespective of baseline B cell marker expression values and clinical response status.

Relationship Between Clinical Response and Baseline Gene Expression Levels

In order to identify gene expression features that were related to the clinical response to treatment we studied the correlation between baseline gene expression level and the clinical response status at 6 months following the start of therapy. For the identification of gene patterns associated with responders status supervised clustering was performed, whereby patients were a priori categorized in predetermined groups based on EULAR response criteria. Genes were selected that differed at least 2-fold in at least 3 samples. When analyzing the gene expression clusters that are determined by the categorization of EULAR responders, moderate responders and nonresponders, we observed a cluster of IFN type I response genes that showed increased expression in the non-responders and a relatively low expression in the responders (FIGS. 1A and B). Additionally patients were ranked based on increasing ΔDAS28 response criteria. Also here, hierarchical cluster analysis learned that a good response (ΔDAS28>1.2) is observed for those patients with a low level of expression of type I IFN response genes at baseline (FIGS. 1A and B). The genes that comprise the IFN response signature are listed in table 2. Comparing the average baseline levels of the IFN response genes shows significant differences between patients with a ΔDAS28>1.2 and those with a ΔDAS28<1.2 (FIG. 2). Relevant genes comprising the IFN signature are represented in tables 2A, B, C and D).

The baseline expression of one of the most pronounced IFN-response genes Mx1 appeared to negatively correlate with the mRNA expression levels of DARC (r=−0.61; P=0.035). Moreover, a positive correlation was observed between Mx1 and the expression of B cell activating factor BAFF (r=0.682; P=0.014).

In addition a number of genes at baseline revealed an increased expression which correlated with a good clinical response (ΔDAS28 or EULAR) (FIG. 1C).

In an independent study the presence of an IFN signature was measured in peripheral blood mononuclear cells from baseline using polymerase chain reaction on the 3 interferon regulated genes Mx1, ISG15 and OAS1. After comparison with healthy controls, patients were qualified as IFN high or IFN low. In the combined AMC and UMCU cohorts (n=50) a significant lower decrease in DAS28 was observed in the IFN high patients (n=24) at week 24 compared to the IFN low group (n=26; mean (±SD) −0.90 (±1.5) compared to −2.0 (±1.4); P=0.012). Accordingly, less patients obtained a EULAR response in the IFN high group compared to the IFN low group when the data are pooled (P=0.032) (FIGS. 3 and 4).

In the UMCU cohort (n=30) also type I serum IFN bioactivity was analyzed using a reporter assay. Serum type I IFN bioactivity at baseline negatively predicted the decrease in DAS28 at week 24 ($R^2$=0.13, P=0.046) (FIG. 5).

Altogether the data reveal that the increased presence of the type I IFN signature before the start of therapy negatively predicts the clinical response to rituximab treatment in RA. These data support the notion that type I IFN signalling plays a role in RA immunopathology.

Moreover higher levels of the following cytokines were measured in the IFNhigh group (P<0.01): IL1β, IL4, IL12, IL13, IL18, IL21, IL23, IFNγ, MIP3β, and more hyaluronic acid (marker of synovial damage) (p=0.005). Also certain cell surface markers such are Sialic acid-binding Ig-like lectin 1 (Siglec-1, sialoadhesin, CD169)) are known as prominent type I IFN-regulated candidate genes. (Biesen et al. (Arthr. Rheum. 2008 April; 58(4):1136-45). We claim the use of Siglec as a marker for IFN activity in RA and for the use of predicting and monitoring therapy response with biologicals Regarding to pharmacodynamics of rituximab in relation to the type I IFN activity, two interesting observations were made in this study. Firstly, non-responders displayed an activated type I IFN-systems already before the start of treatment, which remains active during treatment. Secondly, good responders have low or absent IFN-response activity at baseline and develop IFN-response activity during 3 months of therapy that is comparable to that of non-responders (FIGS. 7 And 8). Factors known to induce type I IFNs and the consecutive induction of IFN-response activity consist of exogenous (infectious) agents and endogenous agents, such as nucleic acids and apoptotic/necrotic material. Hence, a simple explanation for the increase in IFN-response activity during B-cell depletion could be the subsequent release of apoptotic/necrotic material from depleted CD20+ B-cells, which may promote IFN-production and release. The fact that the increase in IFN-response activity does not take place in the IFN high patients might be explained by a saturated and desensitized IFN-system as was previously observed in a subset of patients with multiple sclerosis who are insensitive to the pharmacological and clinical effects of IFN treatment. (van Baarsen L G, Vosslamber S, Tijssen M, Baggen J M, van d, V, Killestein J et al. Pharmacogenomics of interferon-beta therapy in multiple sclerosis: baseline IFN signature determines pharmacological differences between patients. PLoS One 2008; 3(4):e1927 and Comabella M, Lunemann J D, Rio J, Sanchez A, Lopez C, Julia E et al. A type I interferon signature in monocytes is associated with poor response to interferon-beta in multiple sclerosis. Brain 2009; 132(Pt 12): 3353-3365.)

Thus the pharmacological induction of type I IFN-activity could be an important factor in the ameliorative effect of B-cell depletion therapy in RA. Such a role for type I IFN-activity in RA is highlighted by Treschow et al., who showed that IFNβ-deficiency prolonged experimental arthritis.

Additional evidence for a beneficial effect of type I IFNs in RA has been provided by de Hooge et al., who demonstrated that STAT-1 deficiency resulted in exacerbation of experimental arthritis. Moreover, transfer of IFN-competent FLS was able to ameliorate arthritis in IFNβ-deficient recipients (de Hooge et al.). However, although treatment with recombinant-IFNβ revealed promising results in experimental arthritis, treatment of RA patients with IFNβ has been unsuccessful so far, which may be due to issues with dosing and pharmacokinetics as has been suggested by van Holten et al. Our results reveal that the RA patient population may be heterogeneous in relation to the response to type IFNs, separating the population in responders and non-responders based on the baseline differential levels of IFN-response activity at baseline in analogy to findings in multiple sclerosis (Treschow A P, Teige I, Nandakumar K S, Holmdahl R, Issazadeh-Navikas S. Stromal cells and osteoclasts are responsible for exacerbated collagen-induced arthritis in interferon-beta-deficient mice. Arthritis Rheum 2005; 52(12):3739-3748, de Hooge A S, van de Loo F A, Koenders M I, Bennink M B, Arntz O J, Kolbe T et al. Local activation of STAT-1 and STAT-3 in the inflamed synovium during zymosan-induced arthritis: exacerbation of joint inflammation in STAT-1 gene-knockout mice. Arthritis Rheum 2004; 50(6):2014-2023 and van Holten J, Plater-Zyberk C, Tak P P. Interferon-beta for treatment of rheumatoid arthritis? Arthritis Res 2002; 4(6): 346-352.

Change in IFN Response Gene Activity is Related to Baseline Activity and Clinical Response In order to understand the change in IFN response gene activity during therapy we calculated for each patient the ratio of IFN response gene expression pre- vs. post therapy. At three months after therapy we observed an increase in IFN-response gene expression in the non responders (ΔDAS28<1.2), whereas no induction or a decrease was observed in the good responders (ΔDAS28>1.2) (FIG. 6, Table 3).

Association between type I IFN pathway activity and B cell characteristics

The differences in type I IFN pathway activity were related to B cell characteristics at baseline and during treatment in order to determine the possible role of IFN activity in treatment response. No significant correlation was found between baseline gene expression levels of CD19 as a marker for B cell count and baseline type I IFN pathway activity nor treatment induced activity. However, a significant positive correlation was observed between MxA (vergelijking nog even doen met hele IFN cluster) and BAFF (B cell activating factor) at baseline (p=0.0145, r=0.6822) at after 3 months (p=0.0017, r=0.8013). Furthermore, a trend towards a significant positive correlation was observed between BAFF induction and baseline CD19 levels (p=0.0653, r=0.5477), Interestingly, all patients with low CD19 baseline levels show a decrease of BAFF expression after treatment in contrast to the increase that has been described in literature so far.

Genetics and IFN Response Signature

In multiple sclerosis we determined the association of three SNPs and the 30 bp insertion-deletion polymorphism in the IRF5 gene with IFN type I response gene activity at baseline and after pharmacological intervention with IFN-beta. For rs2004640 we showed that patients homozygous for the T allel have a significant higher baseline IFN type I response gene expression (P=0.0198) than heterozygous patients. Accordingly, a significant reduced biological response was observed for patients homozygous for the T allel versus heterozygous patients (P=0.0057) and patients homozygous for the G allel (0.0340). For rs4728142, patients homozygous for the A ellel have a significant higher baseline IFN type I response gene expression (P=0.0394) than heterozygous patients and a trends towards a lower biological response than heterozygous patients (p=0.1198) and homozygous for the G allele (p=0.1421).

We claim the use of rs2004640 and rs4728142 as a marker for IFN activity in RA and for the use of predicting and monitoring therapy response with biologicals. Rs2004640 TT and rs4728142 AA patients are anticipated to have a high baseline IFN level, and thus correspond with a a bad response to BCIDT and/or TCIDT.

TABLE 1

Table 1: List of significant down-regulated genes after Rituximab treatment
Genes that are significantly downregulated by rituximab treatment at 3 (T = 3) and 6 months (T = 6) after the start of therapy
Significantly downregulated genes
FDR < 5%

| T = 0 vs T = 3 | T = 0 vs T = 6 |
|---|---|
| LOC642113 | CD19 |
| FCRLA | CD79A |
| LOC652694 | CD79B |
| CD19 | VPREB3 |
| CD79A | FCRLA |

TABLE 1-continued

Table 1: List of significant down-regulated genes after Rituximab treatment
Genes that are significantly downregulated by rituximab treatment at 3 (T = 3) and 6 months (T = 6) after the start of therapy
Significantly downregulated genes
FDR < 5%

| T = 0 vs T = 3 | T = 0 vs T = 6 |
|---|---|
| VPREB3 | HLADOB |
| CD79B | |
| IGLL1 | |
| LOC652493 | |
| LOC647450 | |
| BLK | |
| HLA-DOB | |
| LOC90925 | |
| CXCR5 | |
| CD72 | |
| LOC653800 | |

TABLE 2A

Genes whose expression at baseline correlated with clinical response (all genes correlation r = 0.6418, selected genes r = 0.8377)

| | correlation 0.6418) | correlation 0.8377 |
|---|---|---|
| Homo sapiens interferon induced transmembrane protein 1 (9-27) (IFITM1), mRNA. | X | |
| Homo sapiens spleen focus forming virus (SFFV) proviral integration oncogene spi1 (SPI1), transcript variant 2, mRNA. | X | |
| Homo sapiens flotillin 1 (FLOT1), mRNA. | X | |
| Homo sapiens ATH1, acid trehalase-like 1 (yeast) (ATHL1), mRNA. | X | |
| Homo sapiens myosin IF (MYO1F), mRNA. | X | |
| Homo sapiens ring finger protein 24 (RNF24), mRNA. | X | |
| Homo sapiens colony stimulating factor 3 receptor (granulocyte) (CSF3R), transcript variant 1, mRNA. | X | |
| wi20e09.x1 NCI_CGAP_Co16 Homo sapiens cDNA clone IMAGE: 2390824 3, mRNA sequence | X | |
| PREDICTED: Homo sapiens ankyrin repeat domain 13 family, member D, transcript variant 7 (ANKRD13D), mRNA. | X | |
| Homo sapiens disrupted in schizophrenia 1 (DISC1), transcript variant S, mRNA. | X | |
| Homo sapiens eukaryotic translation initiation factor 2-alpha kinase 2 (EIF2AK2), mRNA. | X | |
| Homo sapiens 2′,5′-oligoadenylate synthetase 1, 40/46 kDa (OAS1), transcript variant 2, mRNA. | X | |
| Homo sapiens metallothionein 2A (MT2A), mRNA. | X | |
| Homo sapiens metallothionein 1A (MT1A), mRNA. | X | |
| Homo sapiens interferon, alpha-inducible protein 27 (IFI27), mRNA. | X | |
| Homo sapiens peroxisomal proliferator-activated receptor A interacting complex 285 (PRIC285), transcript variant 2, mRNA. | X | X |
| Homo sapiens interferon induced transmembrane protein 3 (1-8U) (IFITM3), mRNA. | X | X |
| Homo sapiens myxovirus (influenza virus) resistance 1, interferon-inducible protein p78 (mouse) (MX1), mRNA. | X | X |
| Homo sapiens myxovirus (influenza virus) resistance 2 (mouse) (MX2), mRNA. | X | X |
| Homo sapiens ISG15 ubiquitin-like modifier (ISG15), mRNA. | X | X |
| Homo sapiens poly (ADP-ribose) polymerase family, member 14 (PARP14), mRNA. | X | X |
| Homo sapiens poly (ADP-ribose) polymerase family, member 12 (PARP12), mRNA. | X | X |
| Homo sapiens lymphocyte antigen 6 complex, locus E (LY6E), mRNA. | X | X |
| Homo sapiens XIAP associated factor 1 (XAF1), transcript variant 2, mRNA. | X | X |
| Homo sapiens 2′-5′-oligoadenylate synthetase 3, 100 kDa (OAS3), mRNA. | X | X |
| Homo sapiens radical S-adenosyl methionine domain containing 2 (RSAD2), mRNA. | X | X |
| Homo sapiens interferon-induced protein 44-like (IFI44L), mRNA. | X | X |
| Homo sapiens hect domain and RLD 5 (HERC5), mRNA. | X | X |
| Homo sapiens interferon-induced protein 44 (IFI44), mRNA. | X | X |
| Homo sapiens epithelial stromal interaction 1 (breast) (EPSTI1), | X | X |

TABLE 2A-continued

Genes whose expression at baseline correlated with clinical response (all genes correlation r = 0.6418, selected genes r = 0.8377)

| | correlation 0.6418) | correlation 0.8377 |
|---|---|---|
| transcript variant 2, mRNA. | | |
| *Homo sapiens* tripartite motif-containing 22 (TRIM22), mRNA. | X | X |
| *Homo sapiens* interferon-induced protein with tetratricopeptide repeats 2 (IFIT2), mRNA. | X | X |
| *Homo sapiens* 2',5'-oligoadenylate synthetase 1, 40/46 kDa (OAS1), transcript variant 3, mRNA, | X | X |
| *Homo sapiens* 2'-5'-oligoadenylate synthetase-like (OASL), transcript variant 2, mRNA. | X | X |
| *Homo sapiens* interferon-induced protein with tetratricopeptide repeats 3 (IFIT3), mRNA. | X | X |
| *Homo sapiens* 2'-5'-oligoadenylate synthetase-like (OASL), transcript variant 1, mRNA. | X | X |
| *Homo sapiens* interferon, alpha-inducible protein 6 (IFI6), transcript variant 2, mRNA. | X | X |
| *Homo sapiens* toll-like receptor 5 (TLR5), mRNA. | X | |
| *Homo sapiens* hypothetical protein LOC153561 (LOC153561), mRNA. | X | |
| *Homo sapiens* hairy and enhancer of split 4 (*Drosophila*) (HES4), mRNA. | X | |

TABLE 2B

Genes whose expression at baseline correlated with clinical response, rated on decreasing fold-difference (<0.7)

| Gene Name | Fold Change |
|---|---|
| IFI44L | 0.166355881 |
| LY6E | 0.200047979 |
| HERC5 | 0.219881515 |
| MX1 | 0.258197325 |
| IFITM3 | 0.307807163 |
| ISG15 | 0.32632231 |
| RSAD2 | 0.328904509 |
| IFI44 | 0.332874976 |
| EPSTI1 | 0.347643012 |
| IFI27 | 0.406435583 |
| HLA-A29.1 | 0.430776913 |
| IFIT3 | 0.46190674 |
| MX2 | 0.465392664 |
| PARP12 | 0.482702435 |
| IFIT2 | 0.488928415 |
| IFIT1 | 0.492501642 |
| MT2A | 0.501691656 |
| OASL | 0.523744525 |
| IFI6 | 0.52553565 |
| HLA-DRB5 | 0.53357054 |
| XAF1 | 0.535434784 |
| SHISA5 | 0.555303959 |
| IFITM1 | 0.562722366 |
| OAS3 | 0.56654893 |
| RNF24 | 0.56658262 |
| RNASE6 | 0.567300967 |
| PRIC285 | 0.573752976 |
| IFI35 | 0.576267343 |
| HES4 | 0.585124581 |
| DHX58 | 0.588144809 |
| OAS1 | 0.590981894 |
| TRIM22 | 0.592527473 |
| EIF2AK2 | 0.59293593 |
| MT1A | 0.593688112 |
| HERC6 | 0.599749038 |
| LOC642113 | 0.60565871 |
| UNC93B1 | 0.606923044 |
| PARP14 | 0.607148187 |
| PGS1 | 0.611341047 |
| NOD2 | 0.61578647 |
| MXD3 | 0.622961487 |
| OAS2 | 0.63323233 |
| HLA-DRB6 | 0.634533297 |
| CST7 | 0.637740886 |
| NRGN | 0.638377805 |
| SAMD9L | 0.639038086 |
| PSCD4 | 0.639293522 |
| ZBP1 | 0.640763582 |
| DAAM2 | 0.640898961 |
| DRAP1 | 0.641305266 |
| SCO2 | 0.647482264 |
| AXUD1 | 0.647813592 |
| SHKBP1 | 0.649862795 |
| JUNB | 0.651382168 |
| ATG16L2 | 0.661673659 |
| STAT2 | 0.66738189 |
| VWF | 0.676393645 |
| NKG7 | 0.677197496 |
| CCDC23 | 0.679387569 |
| SNHG5 | 0.680453694 |
| COL9A2 | 0.680881127 |
| MTHFR | 0.681805694 |
| FAM129A | 0.682221807 |
| HLA-H | 0.682579013 |
| GZMH | 0.683846883 |
| ATHL1 | 0.684490623 |
| REC8 | 0.684860582 |
| CCR1 | 0.68736306 |
| LOC441019 | 0.689004685 |
| RNF19B | 0.691046888 |
| RNF31 | 0.692610518 |
| MOV10 | 0.693790381 |
| FHL3 | 0.694464288 |
| MGC29506 | 0.694847468 |
| MYO1F | 0.695909149 |
| FLOT1 | 0.697032238 |
| HEATR1 | 0.697232166 |
| LOC127295 | 0.699127931 |

TABLE 2C

Genes whose expression at baseline correlated with DAS28 clinical response, rated on increasing q-value (False discovery Rate) from low to high.
Negative genes (12477)

| Row | Gene ID | Gene Name | Score (d) | Numerator (r) | Denominator (s + s0) | Fold Change q |
|---|---|---|---|---|---|---|
| ### | Homo sa | MX1 | −4.6975 | −1.82271783 | 0.388017975 | 0.25819733 |
| ### | Homo sa | SLC39A1 | −4.2454 | −0.44766371 | 0.105446177 | 0.73209284 |
| ### | Homo sa | PARP12 | −4.0456 | −0.96523918 | 0.238591955 | 0.48270244 |
| ### | Homo sa | FAM46A | −3.996 | −0.39267766 | 0.098266835 | 0.75872853 |
| ### | Homo sa | CDCA3 | −3.873 | −0.16733152 | 0.043204261 | 0.89055913 |
| ### | Homo sa | ISG15 | −3.8705 | −1.38614628 | 0.358133408 | 0.32632231 |
| ### | Homo sa | ROPN1 | −3.6612 | −0.15112012 | 0.041276169 | 0.90092235 |
| 828 | Homo sa | APRIN | −3.6376 | −0.13385526 | 0.03679765 | 0.91149505 |
| ### | Homo sa | IFI35 | −3.5776 | −0.77400992 | 0.216348537 | 0.57626734 |
| ### | Homo sa | PERLD1 | −3.5633 | −0.3398056 | 0.095363415 | 0.79017767 |
| ### | Homo sa | IFI6 | −3.4651 | −0.84381226 | 0.243517249 | 0.52553565 |
| ### | Homo sa | C3orf45 | −3.413 | −0.15690841 | 0.045973957 | 0.89593057 |
| ### | Homo sa | DRAP1 | −3.3605 | −0.61539166 | 0.183127065 | 0.64130527 |
| ### | Homo sa | HERC5 | −3.3161 | −1.70094134 | 0.512928623 | 0.21988152 |
| ### | Homo sa | UNC93B1 | −3.2611 | −0.67292986 | 0.206351117 | 0.60692304 |
| ### | Homo sa | DNAL4 | −3.2397 | −0.22124649 | 0.068292385 | 0.85776225 |
| ### | Homo sa | VWF | −3.2374 | −0.5509846 | 0.170194075 | 0.67639364 |
| ### | Homo sa | OR52E8 | −3.2312 | −0.16221585 | 0.050202584 | 0.892805 |
| ### | Homo sa | DHX58 | −3.2028 | −0.6871021 | 0.214533853 | 0.58814481 |
| ### | Homo sa | LY6E | −3.1774 | −1.75159868 | 0.551259429 | 0.20004798 |
| ### | Homo sa | PSCD4 | −3.1563 | −0.61366066 | 0.194423871 | 0.63929352 |
| ### | Homo sa | IFI44L | −3.1512 | −1.87468602 | 0.594906225 | 0.16635588 |
| ### | Homo sa | GLIS2 | −3.1456 | −0.11366149 | 0.036133996 | 0.92388785 |
| ### | Homo sa | MICB | −3.1147 | −0.24775904 | 0.079544977 | 0.84546612 |
| ### | Homo sa | SLC22A18 | −3.0992 | −0.3697264 | 0.119296479 | 0.76484348 |
| ### | Homo sa | REC8 | −3.0966 | −0.50393102 | 0.162738393 | 0.68486058 |
| ### | Homo sa | SHISA5 | −3.0847 | −0.74249111 | 0.240700538 | 0.55530396 |
| ### | Homo sa | IFIT1 | −3.0697 | −0.87499254 | 0.285040268 | 0.49250164 |
| ### | Homo sa | ZHX3 | −3.0423 | −0.23518412 | 0.077304607 | 0.84847007 |
| ### | Homo sa | TAAR2 | −3.0414 | −0.19018096 | 0.062530376 | 0.8738634 |
| ### | Homo sa | C1QB | −3.0386 | −0.39745757 | 0.130801454 | 0.75956256 |
| ### | Homo sa | SP140 | −3.0341 | −0.28941029 | 0.095385657 | 0.81782871 |

TABLE 2D

Genes whose expression at baseline correlated with EULAR clinical response, rated on increasing q-value (False discovery Rate) from low to high.
Negative genes (12420)

| Row | Gene ID | Gene Name | Score (d) | Numerator (r) | Denominator (s + s0) | Fold Change q |
|---|---|---|---|---|---|---|
| ### | Homo sa | MX1 | −6.1654 | −2.00766685 | 0.32563637 | 0.24029237 |
| ### |  | FAM46A | −5.3351 | −0.43801593 | 0.082100555 | 0.73762832 |
| ### | Homo sa | IFI6 | −4.9533 | −0.98759164 | 0.199379682 | 0.48502565 |
| ### | Homo sa | ENDOGL1 | −4.8552 | −0.5112036 | 0.105288981 | 0.69381897 |
| ### | Homo sa | ISG15 | −4.5468 | −1.50668624 | 0.331369405 | 0.30767973 |
| ### | PREDICT | LOC647625 | −4.4746 | −0.14597546 | 0.032623247 | 0.90357645 |
| ### | Homo sa | HERC5 | −4.3101 | −1.94795133 | 0.451954307 | 0.1962335 |
| ### | Homo sa | LDB1 | −4.289 | −0.1989191 | 0.046378744 | 0.87203402 |
| ### | Homo sa | IFI44L | −4.193 | −2.18144028 | 0.520262024 | 0.14559675 |
| ### | Homo sa | IFIT1 | −4.1217 | −1.02242413 | 0.248059141 | 0.4522264 |
| ### | Homo sa | PLEKHM3 | −4.1019 | −0.14725518 | 0.03589937 | 0.9029998 |
| ### | Homo sa | PRIC285 | −4.0879 | −0.89739153 | 0.219526175 | 0.52558882 |
| ### | Homo sa | SHISA5 | −4.0864 | −0.86162284 | 0.210851671 | 0.51702962 |
| ### | Homo sa | DNAL4 | −4.0753 | −0.24648311 | 0.06048229 | 0.8436481 |
| ### | Homo sa | IRF7 | −4.0688 | −0.47695428 | 0.117221322 | 0.70772861 |
| ### | Homo sa | PARP12 | −3.9622 | −0.97835889 | 0.246923753 | 0.48161907 |
| ### | Homo sa | TRIM38 | −3.9522 | −0.46614315 | 0.117944669 | 0.72232255 |
| ### | Homo sa | LY6E | −3.9476 | −1.98139955 | 0.501926109 | 0.17923892 |
| ### | Homo sa | VWF | −3.8407 | −0.60725227 | 0.158109507 | 0.6527704 |
| ### | Homo sa | MX2 | −3.8341 | −1.16524784 | 0.303914936 | 0.41709754 |
| ### | Homo sa | XAF1 | −3.7265 | −0.94385793 | 0.25328038 | 0.48298912 |
| ### | Homo sa | SCGB1C1 | −3.6938 | −0.34168543 | 0.092501515 | 0.78355838 |
| ### | Homo sa | REC8 | −3.6926 | −0.55842049 | 0.151226613 | 0.66127907 |
| ### | Homo sa | CDCA3 | −3.6705 | −0.16584872 | 0.045183879 | 0.89174382 |
| ### | Homo sa | DHX58 | −3.6704 | −0.7479208 | 0.203769311 | 0.56564404 |
| ### | Homo sa | DRAP1 | −3.6451 | −0.65180931 | 0.17882 | 0.62679486 |
| ### | Homo sa | IL17A | −3.566 | −0.15244087 | 0.042748362 | 0.89973967 |
| ### | Homo sa | N4BP1 | −3.5515 | −0.26162486 | 0.073665106 | 0.83226342 |
| 632 | Homo sa | ANKFY1 | −3.5442 | −0.31691827 | 0.089419823 | 0.80127531 |

TABLE 2D-continued

Genes whose expression at baseline correlated with EULAR clinical response, rated on increasing q-value (False discovery Rate) from low to high.
Negative genes (12420)

| Row | Gene ID | Gene Name | Score (d) | Numerator (r) | Denominator (s + s0) | Fold Change q |
|---|---|---|---|---|---|---|
| ### | Homo sa | UNC93B1 | −3.5422 | −0.71441122 | 0.201686145 | 0.59092213 |
| ### | Homo sa | RSAD2 | −3.5387 | −1.43585003 | 0.405755648 | 0.28997959 |
| ### | PREDICT | LOC647046 | −3.5348 | −0.18118739 | 0.051258352 | 0.87993774 |

TABLE 3

Genes whose expression at changed from baseline (T0) till 3 months after therapy (T3) correlated with clinical response (all genes correlation r = 0.5336, selected genes r = 0.7857)

| Ratio T3/T0 | node 377x correlation 0.5336 | node 352x correlation 0.7857 |
|---|---|---|
| *Homo sapiens* interferon, alpha-inducible protein 27 (IFI27), mRNA. | X | |
| *Homo sapiens* 2',5'-oligoadenylate synthetase 1, 40/46 kDa (OAS1), transcript variant 2, mRNA. | X | |
| *Homo sapiens* interferon-induced protein with tetratricopeptide repeats 2 (IFIT2), mRNA. | X | |
| *Homo sapiens* epithelial stromal interaction 1 (breast) (EPSTI1), transcript variant 2, mRNA. | X | X |
| *Homo sapiens* interferon-induced protein 44-like (IFI44L), mRNA. | X | X |
| *Homo sapiens* interferon-induced protein 44 (IFI44), mRNA. | X | X |
| *Homo sapiens* myxovirus (influenza virus) resistance 1, interferon-inducible protein p78 (mouse) (MX1), mRNA. | X | X |
| *Homo sapiens* ISG15 ubiquitin-like modifier (ISG15), mRNA. | X | X |
| *Homo sapiens* lymphocyte antigen 6 complex, locus E (LY6E), mRNA. | X | X |
| *Homo sapiens* interferon induced transmembrane protein 3 (1-8U) (IFITM3), mRNA. | X | X |
| *Homo sapiens* radical S-adenosyl methionine domain containing 2 (RSAD2), mRNA. | X | X |
| *Homo sapiens* hect domain and RLD 5 (HERC5), mRNA. | X | X |
| *Homo sapiens* interferon, alpha-inducible protein 6 (IFI6), transcript variant 3, mRNA. | X | X |
| *Homo sapiens* hairy and enhancer of split 4 (*Drosophila*) (HES4), mRNA. | X | X |
| *Homo sapiens* interferon-induced protein with tetratricopeptide repeats 3 (IFIT3), mRNA. | X | X |
| *Homo sapiens* interferon, alpha-inducible protein 6 (IFI6), transcript variant 2, mRNA. | X | |
| *Homo sapiens* lysozyme (renal amyloidosis) (LYZ), mRNA. | X | |

The invention claimed is:

1. Method for prognosticating the clinical response of a patient suffering from an autoimmune disease to treatment with a soluble B-lymphocyte depleting agent wherein said B-lymphocyte depleting agent is an anti-B cell antibody, said method comprising the steps of
    a) Obtaining at least two samples from said patient wherein a first sample has not been exposed to a soluble B-lymphocyte depleting agent and wherein at least a second sample has been exposed to a soluble B-lymphocyte depleting agent, and wherein said samples comprise cells and serum or plasma,
    b) Determining the level of an IFN-I type response in said at least two samples,
    c) Comparing the level of the IFN-I type response in said first sample with the level of the IFN-I type response in said at least second sample
    d) Prognosticating said clinical response from said comparison, wherein a lower level of IFN-I type response in said first sample in comparison to the level of IFN-type I response in said second sample indicates an increased prospect of a positive clinical response.

2. Method for prognosticating the clinical response of a patient suffering from an autoimmune disease to treatment with a soluble B-lymphocyte depleting agent prior to the start of therapy in a single sample taken prior to the start of therapy, wherein said BCID agent is an anti-B cell antibody, said method comprising the steps of
    a) Obtaining one sample not exposed to a soluble B-lymphocyte depleting agent before the start of treatment with a soluble B-lymphocyte depleting agent, and wherein said sample comprises cells and scrum/plasma serum or plasma,
    b) Determine the level of an IFN-I type response and/or protein metabolism signature (for the latter the increased expression at baseline is associated with a good clinical response),
    c) Comparing the level of the IFN-I type response and/or protein metabolism gene signature (FIG. 1C) in said single sample with the level of the IFN-I type response and/or protein metabolism gene signature (FIG. 1C) in a sample of healthy control individuals, d) Prognosticating said clinical response from said comparison prior to the start of therapy, wherein a higher level of IFN-I type response in said sample in comparison to said sample of healthy control individuals indicates an increased prospect of a poor clinical response.

3. Method according to claim 1 wherein said IFN-I type response level is determined by determining the expression level of BAFF and DARC genes supplemented with at least one gene selected from the group consisting of genes from tables 2A, 2B, 2C, 2D, and 3.

4. Method according to claim 1, wherein the IFN-I type response level is determined by determining the level of an expression product of at least one gene selected from the group consisting of Mx1, ISG15, OAS1, LGALS3BP, RSAD2, IFI44L, IFI44, MX2, OAS2, DARC, BAFF, HERC5, Ly6E, IFI27, RAP1GAP, EPSTI1 and/or SERPING1.

5. Method according to claim 4 wherein the IFN-I type response level is determined by determining the level of an expression product of at least one gene selected from the group consisting of OAS1 and MX2.

6. Method according to claim 3 wherein the IFN-I type response level is determined by determining the level of an expression product of at least one gene selected from the group consisting of RSAD2 and IFI44L.

7. Method according to claim 3 wherein the IFN-I type response level is determined by determining the level of an expression product of at least one gene selected from the group consisting of Mx1, ISG15, OAS2 and SERPING1.

8. Method according to claim 1 wherein said IFN-I type response level is determined by determining the level of an expression product of a gene selected from the group consisting of genes listed in Table 2A, 2B, 2C, 2D, Table 3, BAFF and DARC.

9. Method according to claim 1 wherein said sample comprises cells and serum or plasma from the patient before the start of the therapy to predict the response to said soluble B-lymphocyte depleting agent.

10. Method according to claim 1 wherein said at least a second sample is obtained from an individual between 1 and 8 months after the first exposure of said individual to said soluble B-lymphocyte depleting agent.

11. Method according to claim 1 wherein said at least a second sample is obtained at baseline (simultaneously with sample one prior to the start of therapy) and is exposed in vitro to said soluble B-lymphocyte depleting agent.

12. Method according to claim 1 wherein said at least a second sample has been obtained from a patient that has been exposed to a B-lymphocyte depleting agent.

13. The method of claim 1, wherein the soluble B-lymphocyte depleting agent is rituximab and the autoimmune disease is rheumatoid arthritis.

14. The method of claim 2, wherein the soluble B-lymphocyte depleting agent is rituximab, and the autoimmune disease is rheumatoid arthritis.

15. The method of claim 1, wherein the soluble B-lymphocyte depleting agent reduces B-cell number.

16. The method of claim 2, wherein the soluble B-lymphocyte depleting agent reduces B-cell number.

* * * * *